(12) United States Patent
Sartorelli et al.

(10) Patent No.: US 6,960,568 B2
(45) Date of Patent: Nov. 1, 2005

(54) NUCLEOSIDES AND RELATED PROCESSES, PHARMACEUTICAL COMPOSITIONS AND METHODS

(75) Inventors: Alan C. Sartorelli, Woodbridge, CT (US); Yung-Chi Cheng, Woodbridge, CT (US); Mao-Chin Liu, North Haven, CT (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 10/321,133

(22) Filed: Dec. 17, 2002

(65) Prior Publication Data

US 2004/0116362 A1 Jun. 17, 2004

(51) Int. Cl.[7] ..................... C07H 19/22; A61K 31/7052
(52) U.S. Cl. ..................... 514/43; 514/45; 514/256; 514/269; 514/274; 514/300; 536/25.3; 536/28.1; 536/28.2; 536/28.4; 536/28.5; 536/22.1; 536/24.3; 536/24.5; 536/26.23; 536/26.26; 536/26.7; 536/26.8; 536/27.14; 536/28.54; 544/314
(58) Field of Search ..................... 514/43, 45, 256, 514/269, 274, 300; 536/25.3, 28.1, 28.2, 28.4, 28.5, 22.1, 24.31, 24.5, 26.73, 26.7, 26.8, 87.16, 27.14, 28.54; 544/314

(56) References Cited

U.S. PATENT DOCUMENTS

| 4,381,344 | A | * | 4/1983 | Rideout et al. | ............... | 435/87 |
| 6,211,158 | B1 | * | 4/2001 | Seela et al. | ............... | 514/44 |
| 6,455,506 | B1 | * | 9/2002 | Townsend et al. | ............ | 514/43 |

OTHER PUBLICATIONS

Minakawa et al. J. Org.Chem. 64, 7158–7172, 1999.*
Rousseau, Robert J. et al.; The Synthesis of 4–Amino–β–D–ribofuranosylimidazo (4,5–c) pyridine (3–Deazaadenosine) and Related Nucleotides; Biochemistry; pp 756–760, 1966.
Montgomery, John A. et. al; 3–Deaza–6–methylthiopurine Ribonucleoside[1];vol. 9; pp 105–107, 1966.
Rousseau, Robert J., et al; The Synthesis of 3–Deaze–6–thioguanine and Certain Related Derivatives; Apr. 1974; vol. 11; pp. 233–235.
May, Jesse A, et. al; A General Synthesis of 4–Substituted 1–(β–o–Ribofuranosyl) imidazo–(4,5–c) pyridines +; 1975, J.C.S. Perkin; pp 125–129.

(Continued)

*Primary Examiner*—James O. Wilson
*Assistant Examiner*—Devesh Khare
(74) *Attorney, Agent, or Firm*—Henry D. Coleman; R. Nell Sudol; William J. Sapone

(57) ABSTRACT

The invention provides novel nucleosides and related processes, pharmaceutical compositions, and methods. The novel nucleosides are useful in a wide variety of antiviral, antineoplastic, and antibacterial applications. Preferred embodiments of the instant invention include novel 2 halogen-substituted, 3 halogen-substituted, and 2',3'dihalogen-substituted analogues of 3-deazaadenosine, and novel 3 halogen-substituted analogues of 3-deazaguanosine. Compounds of the instant invention, including 4-Amino-6-fluoro-1-(β-D-ribofuranosyl)imidazo [4,5-c]pyridine and 6-Amino-7-bromo-1,5-dihydro-1-β-D-ribofuranosylimidazo[4,5-c]pyridin-4-one, have exhibited potent antiviral and anticancer activity in vitro. The compounds are also useful in the concomitant treatment of bacterial infections associated with viral infections such as AIDS.

2 Claims, 6 Drawing Sheets

Scheme 1

OTHER PUBLICATIONS

Cook, P. Dan, et. al; A New Class of Potent Guanine Antimetabolites. Synthesis of 3–Deazaguanine, 3–Deazaguanosine, and 3–Deazaguanylic Acid by a Novel Ring Closure or Imidazole Precursors; May 14, 1975; Journal of American Chemical Society; pp 2916, 2917.

May, Jesse A. et al.; Synthesis of 6–Amino–1–(β–D–Ribofuranosyl) Imidazo [4,5–c]–Pyridin–4–Thione (3–Deaza–6–Thioguanosine) and Certain Related Derivatives$_1$ ; 1975; pp 371–394.

Cook, P. Dan et al; Synthesis of 3–Deazaguanine, 3–Deazaguanosine, and 3–Deazaguanylic Acid by a Novel Ring Closure of Imidazole Precursors; Mar. 17, 1976; Journal of the American Chemical Society; pp 1492–1498.

Montgomery, John A. et al.; A Comparison of Two Methods for the Preparation of 3–Deazapurine Ribonucelosides; Apr., 1977; vol. 14; pp 195–197.

Chiang, Peter K. et al.; S–Adenosyl–τ—honocysteine Hydrolase: Analogues of S–Adensoyl–τ—homocysteine as Potential Inhibitors; May 19, 1977; Molecular Pharmacology; pp 393–947.

May, Jesse A. et al.; Synthesis of 6–Amino–1–(β–D–Ribofuranosyl) Imidazo [4,5–c]–Pyridin–4–Thione (3–Deaza–6–Thioguanosine) and Certain Related Derivatives[1]; 1975; pp 371–394.

Cook, P. Dan et al.; Synthesis of 3–Deazaguanine, 3–Deazaguanosine, and 3–Deazaguanylic Acid by a Novel Ring Closure of Imidazole Precursors; Mar. 17, 1976; Journal of the American Chemical Society; pp 1492–1498.

Montgomery, John A. et al.; A Comparison of Two Methods for the Preparation of 3–Deazapurine Ribonucelosides; Apr., 1977; vol. 14; pp 195–197.

Chiang, Peter K. et al.; S–Adenosyl–τ—honocysteine Hydrolase: Analogues of S–Adensoyl–τ—homocysteine as Potential Inhibitors; May 19, 1977; Molecular Pharmacology; pp 939–947.

Allen, Louis B. et al.; Antiviral Activity of 3–Deazaguanine, 3–Deazaguanosine, & 3–Deazaguanylic Acid; Antimicrobial Agents and Chemothreapy; Jul., 1977; vol. 12, No. 1; pp 114–119.

Cook, Dan P. et al.; Synthesis of 7–and 9–β–D– Ribofuranosides of 3–Deaza–6–thioguanine and 3–Deaza–2,6–diaminopurine by a Novel Ring Closure of 4(5)–Cyano–5(4)–cynnomethylimidazole β–D– Ribofuranosides; 1978; J. Org. Chem.; vol. 43, No. 2; pp 289–293.

Chiang, Peter K. et al.; Adenosylhomocysteine inhibitors: Synthesis of 5'–deoxy—5'—(isobutylthio)–3–deazaadenosine and its effect on *Rous sarcoma* virus and Gross murine leukemia virus; May 30, 1978; Biochemical and Biophysical Research Communications; vol. No. 82, No. 2; pp 417–423.

Bader, John P. et al.; 3–Deazaadenosine, an Inhibitor of Adenosylhomocysteine Hydrolase Inhibits Reproduction of *Rous sarcoma* virus and Transformation of Chick Embryo Cells; 1978; Virology; pp 494, 360–365, 1063.

Poonian, Mohibdar S, et al; Synthesis of Arabinofuranosyl Derivatives of 3–Deazaguanine; 1979; Journal of Medical Chemistry; vol. 22, No. 8; pp 958–962.

Streeter, David G., et al.; 7–Ribosyl–3–Deazaguanine–Mechanism of Antibacterial Action; 1980; Biomedical Pharmacology; vol. 29; pp 1791–1797.

Guranowski, Andrzej, et al; Adenosine Analogues as Substrates and Inhibitors of S–Adenosylhomocusteine Hydrolase; 1981; American Chemical Society; pp 110–115.

Actions of 3–deazaguanine and 3–deazaguanosine on variant lines of Chinese hamster ovary cells; 1981; Biochemical Pharmacology; vol. 30, No. 16; pp 2374–2376.

Bodner, Ann J., et al; Anti–Viral Activity of 3–Deazaadenosine and 5'–Deoxy–5'–Isobutylthio–3–Deazaadenosine (3–deaza–SIBA); Jan. 30, 1981; Biochemical and Biophysical Research Communications; vol. 98, No. 2; pp 476–481.

Khwaja, Tasneem A.; 3–Deazaguanine, a Candidate Drug for the Chemotherapy of Breast Carcinomas?; Oct., 1982; Cancer Treatment Reports; vol. 66, No. 10; pp 1853–1858.

Montgomery, J.A., et al; 1–β–D–Arabinofuranosyl–1–H–inidazo [4,5–,] pyridine (ara–3–Deazaadenine); 1981; American Chemical Society; pp 96–98.

Mian, A. Mohsin, et al; Synthesis and Antitumor Activity of 2–Deoxyribofuranosides of 3–Deazaguanine; 1983; American Chemical Society; pp 286–291.

Revankar, Ganapathi, R., et al; Synthesis and Antiviral/Antitumor Activities of Certain 3–Deazaguanine Nucleosides and Nucleotides; 1984; American Chemical Society; pp 1389–1396.

Gupta, Pranab K., et al; A new synthesis of certain 7–(β–D–ribofuranosyl) and 7–(2–deoxy–β–D–ribofuranosyl)and 7–(2–deoxy–β–D–ribofuranosyl) derivatives of 3–deazaguanine via the sodium salt glycosylation procedure; 1985; Nucleic Acids Research; vol. 13, No. 14; pp 5341–5352.

Berry, David A. et al; Synthesis of 8–Amino–3–deazaguanine via Imidazole Precursors. Antitumor Activity and Inhibition of Purine Nucleoside Phosphorylase; 1986; J. Med. Chem.; pp 2034–2037.

Krenitsky, Thomas K. et al; Imidazo [4,5–c] pyridines (3–Deazapurines) and Their Nucleosides as Immunosuppressive and Antiiflammatory Agents; 1986; J. Med. Chem.; pp 138–143.

Mian, A. Mohsin, et al; Antitumor Activity and Mechanism of Action of 6–Thio–3–deazaguanine; Apr. 1, 1987; Cancer Research 47; pp 1863–1866.

Bennett, L. Lee, et al; Alterations in Nucleotide Pools Induced by 3–Deazaadenosine and Related Compounds; 1988; Biochemical Pharmology; vol. 37, No. 7; pp 1233–1244.

McGee, Danny P.C., et al; Synthesis and Antiviral Activity of the 3–Deaza Analogue of 9–((1, 3–Dihydroxy–2–Propoxy)Methyl) Guanine; 1990; Nucleosides & Nucleotides; pp 815–826.

Serafinowski, Pawel; Synthesis of 2',3'–Dideoxy–3–deazaadenosine and Some of its Analogues; Sep., 1990; pp 757–760.

Seels, Frank, et al; 173.3–Deazaguanine N7–and N9–(2'–Deoxy–β–D–ribofuranosides): Building Blocks for Solid–Phase Synthesis and Incorporation into Oligodeoxyribonucelotides; 1991; Helvetica Chmica Acta; vol. 74; pp1790–1800.

Minakawa, Noriaki et al; Nucleosides and Nucleotides. 114. A Convenient Method for the Synthesis of 3–Deazapurine Nucleosides from AICA–Ribsode[1]; 1994; Tetrahedron Letters, vol. 34, No. 4; pp 661–664.

Acevedo, Oscar, L., et al; Synthesis of Several 2'–Deoxy–3–Alkyl(Aryl)–3–Deazaguanosines: Mild Alkylation of a Cyanomethyl Imidazole with Electrophiles; 1993; Nucleosides and Nucleotides; pp 403–416.

Siddiqi, Suhaib, M. et al; 3–Deaza–5'–noraristeromycin and Their Antiviral Properties; 1995; Journal of Medical Chemistry; vol. 38, No. 6; pp 1035–1038.

* cited by examiner

Scheme 1

Scheme 2

Scheme 3

Scheme 4

Scheme 5

Scheme 6

NUCLEOSIDES AND RELATED PROCESSES, PHARMACEUTICAL COMPOSITIONS AND METHODS

FIELD OF THE INVENTION

The invention provides novel nucleosides and related processes, pharmaceutical compositions, and methods. The novel nucleosides are useful in a wide variety of antiviral, antineoplastic, and antibacterial applications. Preferred embodiments of the instant invention include novel 2 halogen-substituted, 3 halogen-substituted, and 2',3'dihalogen-substituted analogues of 3-deazaadenosine, and novel 3 halogen-substituted analogues of 3-deazaguanosine. Compounds of the instant invention, including 4-Amino-6-fluoro-1-(β-D-ribofuranosyl)imidazo[4,5-c]pyridine and 6-Amino-7-bromo-1,5-dihydro-1-β-D-ribofuranosylimidazo[4,5-c]pyridin-4-one, have exhibited potent antiviral and anticancer activity in vitro. The compounds are also useful in the concomitant treatment of bacterial infections associated with viral infections such as AIDS.

BACKGROUND OF THE INVENTION

Considerable progress has been made in developing nucleosides with anticancer and/or antiviral activity by modifying the base portion of a nucleoside. For example, 3-deazaadenosine, a potent inhibitor of adenosylhomocysteine hydrolase, has been shown to have significant activity against herpes simplex virus type-1, human immunodeficiency virus and oncogenic DNA viruses. Bodner, A. J.; Cantoni, G. L.; Chiang, P. K. Biochem. Biophys. Res. Commun. 1981 98, 476–481. Flexner, C. W.; Hildreth, J. E.; Kuncl, R. W.; Drachman, D. B. Lancet 1992 339, 438. Bader, J. P.; Brown, N. R.; Chiang, P. K.; Cantoni, G. L. Virology 1978 89, 494–505. Chiang, P. K.; Cantoni, G. L.; Bader, J. P.; Shannon, W. M.; Thomas, H. J.; Montgomery, J. A. Biochem. Biophys. Res. Commun. 1978 82 417–423. 3-Deazaguanosine has been reported to possess broad spectrum antiviral activity against a variety of DNA and RNA viruses, as well as antitumor activity against the L1210 leukemia and several mammary adenocarcinomas in mice. Allen, L. B.; Huffman, J. H.; Cook, P. D.; Meyer, R. B., Jr.; Robins, R. K.; Sidwell, R. W. Antimicrob. Agents Chemother. 1977 12, 114–119. Saunders, P. P.; Chao, L. Y.; Loo, T. L.; Robins, R. K. Biochem. Pharmacol. 1981 30, 2374–2376. Revankar, G. R.; Gupta, P. K.; Adams, A. D.; Dalley, N. K.; McKernan, P. A.; Cook, P. D.; Canonico, P. G.; Robins, R. K. J. Med. Chem., 1984 27, 1389–1396.

Certain 2-halogen-substituted purine nucleosides have exhibited cytotoxicity in vitro and anticancer activity in vivo. Carson, D. A.; Wasson, D. B.; Kaye, J.; Ullman, B.; Martin, D. W., Jr.; Robins, R. K.; Montgomery, J. A. Proc. Natl. Acad. Sci. USA 1980 77, 6865–6869. Hutton, J. J.; Von Hoff, D. D.; Kuhn, J.; Phillips, J.; Hersh, M.; Clark, G. Cancer Res. 1984 44, 4183–4186. Secrist, J. A., III; Shortnacy, A. T.; Montgomery, J. A. J. Med. Chem. 1988 31, 405–410. Montgomery, J. A.; Shortnacy-Fowler, A. T.; Clayton, S. D.; Riordan, J. M.; Secrist, J. A., III. J. Med. Chem. 1992 35, 397–401. Among these analogues, Fludarabine phosphate (9-β-D-arabinofuranosyl-2-fluoroadenine 5'-O-phosphate) and Cladribine (2-chloro-2'-deoxy-β-D-adenosine) are currently used as anticancer agents.

However, notwithstanding the progress that has been made in identifying nucleosides having anticancer and/or antiviral activity, the need exists for biologically-active nucleosides that exhibit a wide range of antiviral and/or anticancer properties and that may be employed in antiviral and anticancer pharmaceutical compositions. Such nucleosides must be safe and well-tolerated and be suitable for use in numerous pharmaceutical dosage forms and routes of administration. Preferably, such nucleosides would exhibit both antineoplastic and antiviral activity upon administration to a patient in need, and would also be useful in treating bacterial infections such as tuberculosis and associated viral infections such as AIDS.

OBJECTS OF THE INVENTION

It is an object of the instant invention to provide novel, biologically-active nucleosides useful in a wide range of antiviral, antineoplastic, and antibacterial applications.

It is a further object of the instant invention to provide novel, biologically-active nucleosides that may be employed in antiviral and anticancer pharmaceutical compositions and which are also effective against bacterial infections and bacterial infections associated with viral infections such as AIDS.

It is a further object of the instant invention to provide novel, biologically-active nucleosides that are safe and well-tolerated.

It is a further object of the instant invention to provide methods of using novel, biologically-active nucleosides to treat viral, bacterial and neoplastic conditions.

It is a further object of the instant invention to provide novel processes for making novel, biologically-active nucleosides.

SUMMARY OF THE INVENTION

In accordance with the above stated objects, the instant invention provides novel nucleosides of the formula (I):

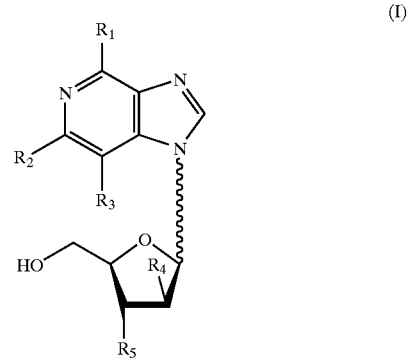

and anomers, pharmaceutically acceptable salts, solvates, or polymorphs thereof where $R^1$, $R^2$ and $R^3$ are selected from OH, SH, NRR' or a halogen group (F, Cl, Br or I); $R^4$ and $R^5$ are selected from H, OH, a halogen group or together form an unsaturated double bond between the 2' and 3' positions (i.e., the carbons to which $R^4$ and $R^5$ are attached); and R and R' are independently selected from H or a $C_1$–$C_3$ alkyl group. The invention also provides antiviral, bacterial and antineoplastic (including anticancer) pharmaceutical compositions comprising the novel nucleosides, methods of using these pharmaceutical compositions to treat a wide variety of viral, bacterial and neoplastic conditions, and processes for making the novel nucleosides.

The beta-anomer of compounds of formula (I) is preferred, and that anomer is illustrated below in formula (II):

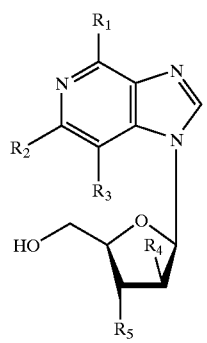

(II)

Preferred nucleosides of the instant invention include compounds of the following formulae (III) through (X):

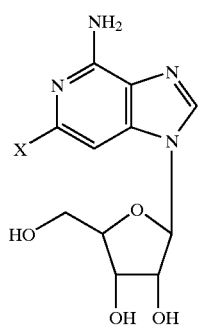

(III)

where X is a halogen group (F, Cl, Br or I);

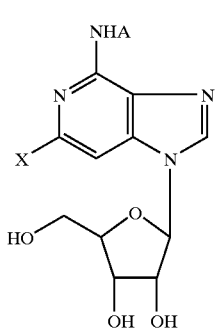

(IV)

where X is a halogen group (F, Cl, Br or I) and A is an alkyl group;

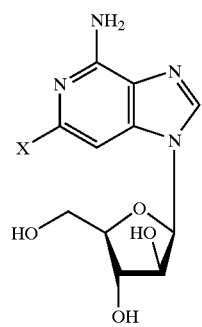

(V)

where X is a halogen group (F, Cl, Br or I);

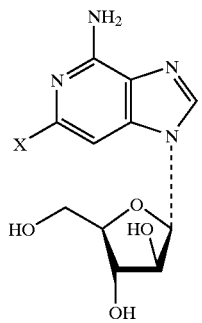

(VI)

where X is a halogen group (F, Cl, Br or I);

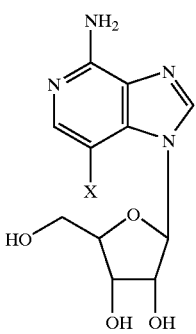

(VII)

where X is a halogen group (F, Cl, Br or I);

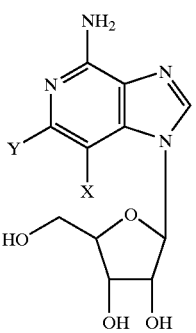

(VIII)

where X and Y are the same or different and are a halogen group (F, Cl, Br or I);

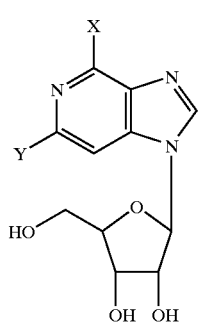

(IX)

where X and Y are the same or different and are a halogen group (F, Cl, Br or I); and

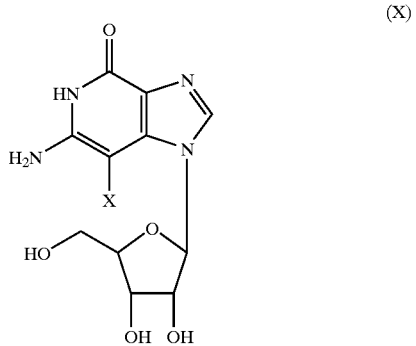

(X)

where X is a halogen group (F, Cl, Br or I).

Preferred nucleosides of the instant invention therefore include:
4-Amino-6-fluoro-1-(β-D-ribofuranosyl)imidazo[4,5-c]pyridine;
6-Fluoro-4-methylamino-1-(β-D-ribofuranosyl)imidazo[4,5-c]pyridine;
4-Amino-6-fluoro-1-β-D-arabinofuranosylimidazo[4,5-c]pyridine;
4-Amino-6-fluoro-1-α-D-arabinofuranosylimidazo[4,5-c]pyridine;
4-Amino-7-fluoro-1-(β-D-ribofuranosyl)imidazo[4,5-c]pyridine;
4-Amino-7-chloro-1-(β-D-ribofuranosyl)imidazo[4,5-c]pyridine;
4-Amino-6,7-difluoro-1-(β-D-ribofuranosyl)imidazo[4,5-c]pyridine;
4-Amino-6,7-difluoro-3-(β-D-ribofuranosyl)imidazo[4,5-c]pyridine;
4-Amino-7-chloro-6-fluoro-1-(β-D-ribofuranosyl)imidazo[4,5-c]pyridine;
4-Amino-7-chloro-6-fluoro-3-(β-D-ribofuranosyl)imidazo[4,5-c]pyridine;
6-Amino-7-chloro-1,5-dihydro-1-β-D-ribofuranosylimidazo[4,5-c]pyridin-4-one; and
6-Amino-7-bromo-1,5-dihydro-1-β-D-ribofuranosylimidazo[4,5-c]pyridin-4-one.

Particularly preferred nucleosides of the instant invention include:
4-Amino-6-fluoro-1-(β-D-ribofuranosyl)imidazo[4,5-c]pyridine;
4-Amino-7-fluoro-1-(β-D-ribofuranosyl)imidazo[4,5-c]pyridine;
4-Amino-6,7-difluoro-1-(β-D-ribofuranosyl)imidazo[4,5-c]pyridine;
4-Amino-6,7-difluoro-3-(β-D-ribofuranosyl)imidazo[4,5-c]pyridine;
4-Amino-7-chloro-6-fluoro-1-(β-D-ribofuranosyl)imidazo[4,5-c]pyridine;
6-Amino-7-chloro-1,5-dihydro-1-β-D-ribofuranosylimidazo[4,5-c]pyridin-4-one; and
6-Amino-7-bromo-1,5-dihydro-1-β-D-ribofuranosylimidazo[4,5-c]pyridin-4-one.

Of these seven nucleosides of the instant invention, 4-Amino-6-fluoro-1-(β-D-ribofuranosyl)imidazo[4,5-c]pyridine and 6-Amino-7-bromo-1,5-dihydro-1-β-D-ribofuranosylimidazo[4,5-c]pyridin-4-one are especially preferred.

The novel nucleosides of the instant invention have a broad spectrum of antiviral and antineoplastic (including anticancer) activity. As defined further hereinafter, an antineoplastic agent is an agent that is antagonistic to the growth of a neoplasm. For example, as disclosed in detail hereinafter, 4-Amino-6-fluoro-1-(β-D-ribofuranosyl)imidazo[4,5-c]pyridine, 4-Amino-7-fluoro-1-(β-D-ribofuranosyl)imidazo[4,5-c]pyridine, 4-Amino-6,7-difluoro-1-(β-D-ribofuranosyl)imidazo[4,5-c]pyridine, and 4-Amino-7-chloro-6-fluoro-1-(β-D-ribofuranosyl)imidazo[4,5-c]pyridine have proven active in vitro against some or all of the following neoplastic cell lines: L1210 and P388 leukemias, the CCRF-CEM lymphoblastic leukemia, and the $B_{16}F_{10}$ melanoma cell lines. The novel 3 halogen substituted analogues of 3-deazaguanosine of the instant invention, 6-Amino-7-chloro-1,5-dihydro-1-β-D-ribofuranosylimidazo[4,5-c]pyridin-4-one and 6-Amino-7-bromo-1,5-dihydro-1-β-D-ribofuranosylimidazo[4,5-c]pyridin-4-one have also proven active in vitro against these neoplastic cell lines.

The present invention also relates to methods for inhibiting the growth, replication or elaboration of a virus population and for treating a variety of virus infections, including, for example, human immunodeficiency viruses 1 and 2 (HIV-1 and HIV-2), human T-cell leukemia viruses 1 and 2 (HTLV-1 and HTLV-2), respiratory syncytial virus (RSV), human papilloma virus (HPV), adenovirus, hepatitis B virus (HBV), hepatitis C virus (HCV), Epstein-Barr virus (EBV), varicella zoster virus (VZV), cytomegalovirus (CMV), herpes simplex viruses 1 and 2 (HSV-1 and HSV-2), human herpes virus 8 (HHV-8, also known as Kaposi's sarcoma-associated virus) and flaviviruses, including Yellow Fever virus, Dengue virus, Japanese Encephalitis and West Nile viruses, said method comprising administering an antiviral effective amount of a composition according to the present invention to a patient in need thereof to treat, prevent or reduce the likelihood of contracting a viral infection.

The invention provides methods of use relating to treatment of infections caused by viruses, including, for example, human immunodeficiency viruses 1 and 2 (HIV-1 and HIV-2), human T-cell leukemia viruses 1 and 2 (HTLV-1 and HTLV-2), respiratory syncytial virus (RSV), human papilloma virus (HPV), adenovirus, hepatitis B virus (HBV), hepatitis C virus (HCV), Epstein-Barr virus (EBV), varicella zoster virus (VZV), cytomegalovirus (CMV), herpes simplex viruses 1 and 2 (HSV-1 and HSV-2), human herpes virus 8 (HHV-8, also known as Kaposi's sarcoma-associated virus) and flaviviruses, including Yellow Fever virus, Dengue virus, Japanese Encephalitis and West Nile viruses. For example, the novel compounds 4-Amino-7-fluoro-1-(β-D-ribofuranosyl)imidazo[4,5-c]pyridine, 4-Amino-6,7-difluoro-3-(β-D-ribofuranosyl)imidazo[4,5-c]pyridine, and 4-Amino-7-chloro-6-fluoro-1-(β-D-ribofuranosyl)imidazo[4,5-c]pyridine showed particular activity in vitro against Hepatitis B virus.

The invention also provides a method of making 2-halogen-substituted analogues of 3-deazaadenosine by reacting halogen-substituted imidazo[4,5-c]pyridines with excess hexamethyldisilazane and a catalytic amount of ammonium sulfate to yield a trimethylsilyl derivative, which is reacted with 1-O-acetyl-2,3,5-tri-O-benzoyl-D-ribofuranose in an organic solvent such as 1,2-dichloroethane using a Lewis acid such as trimethylsilyl trifluoromethanesulfonate (TMSOTf) as a catalyst at around room temperature to give a tribenzoyl-protected nucleoside derivative. This derivative is reacted with either saturated ethanolic ammonia or 40% methylamine to yield the 2-halogen-substituted analogue of 3-deazaadenosine. For example, the invention provides a method of making 4-Amino-6-fluoro-1-(β-D-ribofuranosyl)imidazo[4,5-c] pyridine by reacting 4,6-Difluoroimidazo[4,5-c]pyridine with excess hexamethyldisilazane and a catalytic amount of ammonium sulfate to yield a trimethylsilyl derivative, which is reacted with 1-O-acetyl-2,3,5-tri-O-benzoyl-β-D-ribofuranose in 1,2-dichloroethane using TMSOTf as a catalyst at room temperature to give a tribenzoyl-protected nucleoside derivative, which in turn is reacted with either saturated ethanolic ammonia or 40% methylamine to yield 4-Amino-6-fluoro-1-(β-D-ribofuranosyl)imidazo[4,5-c] pyridine.

The invention also provides a method of making 2-halogen-substituted analogues of 3-deazaadenosine by reacting halogen-substituted imidazo[4,5-c]pyridines with excess hexamethyldisilazane to yield a trimethylsilyl derivative, which is treated with 2,3,5-tri-O-benzyl-1-O-(4-nitro-benzoyl)-β-D-arabinofuranose in 1,2-dichloroethane using TMSOTf as a catalyst at room temperature under nitrogen to yield a mixture of α- and β-nucleosides. The mixture of α- and β-nucleosides is treated with ammonia saturated ethanol to yield a 4-amino derivative. The 4-amino derivative undergoes debenzylation with palladium (II) oxide hydrate and cyclohexene in ethanol to yield the 2-halogen-substituted analogues of 3-deazaadenosine. For example, the invention provides a method of making 4-Amino-6-fluoro-1-β-D-arabinofuranosylimidazo[4,5-c]pyridine and 4-Amino-6-fluoro-1-α-D-arabinofuranosylimidazo[4,5-c]pyridine by reacting 4,6-Difluoroimidazo[4,5-c]pyridine with excess hexamethyldisilazane to yield the trimethylsilyl derivative, which is treated with 2,3,5-tri-O-benzyl-1-O-(4-nitro-benzoyl)-D-arabinofuranose in 1,2-dichloroethane using TMSOTf as a catalyst at room temperature under nitrogen to yield a mixture of α- and β-nucleosides. The α- and β-nucleosides are treated with ammonia saturated ethanol to yield the 4-amino derivatives, which undergo debenzylation with palladium (II) oxide hydrate and cyclohexene in ethanol to yield 4-Amino-6-fluoro-1-β-D-arabinofuranosylimidazo[4,5-c]pyridine and 4-Amino-6-fluoro-1-α-D-arabinofuranosylimidazo[4,5-c]pyridine.

The invention also provides a method of making 3-halogen-substituted analogues of 3-deazaadenosine by condensing silylated 4,7 dihaloimidazo[4,5-c]pyridines with 1-O-acetyl-2,3,5-tri-O-benzoyl-β-D-ribofuranose in an organic solvent such as 1,2-dichloroethane and in the presence of TMSOTf to yield 3-deaza-3-halogen-substituted purine nucleosides, which are deblocked with sodium methoxide in methanol to yield corresponding nucleoside derivatives. These derivatives are treated with anhydrous hydrazine, and the reaction product is catalytically hydrogenated to yield 3-halogen-substituted analogues of 3-deazaadenosine. For example, the invention provides a method of making 4-Amino-7-fluoro-1-(β-D-ribofuranosyl) imidazo[4,5-c]pyridine and 4-Amino-7-chloro-1-(β-D-ribofuranosyl)imidazo[4,5-c]pyridine by condensation of silylated 4-chloro-7-fluoroimidazo[4,5-c]pyridine and silylated 4,7-dichloroimidazo[4,5-c]pyridine with 1-O-acetyl-2, 3,5-tri-O-benzoyl-β-D-ribofuranose in 1,2-dichloroethane in the presence of TMSOTf to yield 3-deaza-3-halogen-substituted purine nucleosides. The nucleosides are deblocked with sodium methoxide in methanol to yield the corresponding nucleoside derivatives. These derivatives are treated with anhydrous hydrazine, and the reaction product is catalytically hydrogenated to yield either 4-Amino-7-fluoro-1-(β-D-ribofuranosyl)imidazo[4,5-c]pyridine or 4-Amino-7-chloro-1-(β-D-ribofuranosyl)imidazo[4,5-c] pyridine.

The invention also provides a method of making 6,7-dihalogen-substituted analogues of 3-deazaadenosine by condensation of a silylated 4,6,7-trihaloimidazo[4,5-c] pyridine or a silylated 7-halo-4,6-dihaloimidazo[4,5-c] pyridine with 1-O-acetyl-2,3,5-tri-O-benzoyl-β-D-ribofuranose in an organic solvent such as 1,2-dichloroethane and in the presence of a Lewis acid such as TMSOTf to yield the corresponding protected 1-ribosides and 3-ribosides. Treatment of these ribosides with ammonia saturated ethanol yields the 6,7-dihalogen-substituted analogues of 3-deazaadenosine. For example, the invention provides a method of making 4-Amino-6,7-difluoro-1-(β-D-ribofuranosyl)imidazo[4,5-c]pyridine and 4-Amino-7-chloro-6-fluoro-1-(β-ribofuranosyl)imidazo[4,5-c]pyridine by condensing silylated 4,6,7-trifluoroimidazo[4,5-c] pyridine and silylated 7-chloro-4,6-difluoroimidazo[4,5-c] pyridine with 1-O-acetyl-2,3,5-tri-O-benzoyl-β-D-ribofuranose in 1,2-dichloroethane and in the presence of TMSOTf to yield the corresponding protected 1-ribosides and 3-ribosides. Treatment of these ribosides with ammonia saturated ethanol yielded 4-Amino-6,7-difluoro-1-(β-D-ribofuranosyl)imidazo[4,5-c]pyridine or 4-Amino-7-chloro-6-fluoro-1-(β-D-ribofuranosyl)imidazo[4,5-c]pyridine. 4-Amino-6,7-difluoro-3-(β-D-ribofuranosyl)imidazo[4,5-c] pyridine and 4-Amino-7-chloro-6-fluoro-3-(β-D-ribofuranosyl)imidazo[4,5-c]pyridine can be made in the same way.

The invention also provides a method of making 3-halogen-substituted analogues of 3-deazaguanosine by halogenation of 3-deazaguanosine. For example, the invention provides a method of making 6-Amino-7-chloro-1,5-dihydro-1-β-D-ribofuranosylimidazo[4,5-c]pyridin-4-one and 6-Amino-7-bromo-1,5-dihydro-1-β-D-ribofuranosylimidazo[4,5-c]pyridin-4-one by halogenation of 3-deazaguanosine.

Synthesis of the novel compounds of the instant invention, and methods of making and using the compounds in a broad ranges of pharmaceutical compositions and uses, are illustrated further in the following detailed description.

Figure 1:
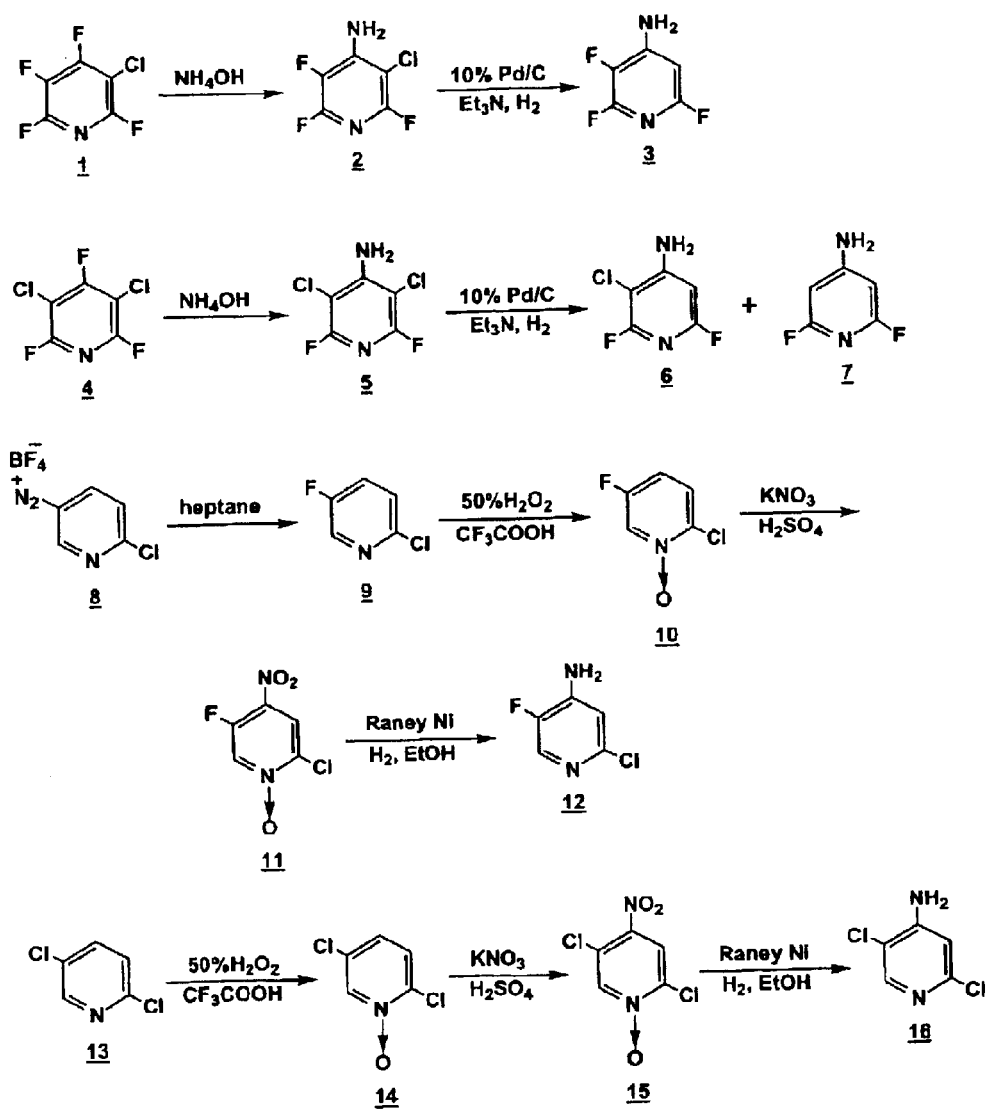
FIG. 1 illustrates the synthesis of various halogen-substituted 4-aminopyridines useful as intermediates in making novel nucleosides of the instant invention.

[4,5-c]pyridin-4-one and 6-Amino-7-bromo-1,5-dihydro-1-β-D-ribofuranosylimidazo[4,5-c]pyridin-4-one.

DETAILED DESCRIPTION OF THE INVENTION

As used herein, the following terms have the following respective meanings.

The term "alkyl" as used herein, unless otherwise indicated, includes saturated and monovalent $C_1$ to $C_6$, preferably, $C_1$ to $C_6$ hydrocarbon radicals having straight, branched, or cyclic moieties or combinations thereof.

The term "anomer" as used herein means one of a pair of isomers of a cyclic carbohydrate resulting from creation of a new point of symmetry when a rearrangement of atoms occurs at an aldehyde or ketone position.

The term "one or more substituents" as used herein refers to a number of substituents that equals from one to the maximum number of substituents possible based on the number of available bonding sites.

"2' and 3' positions" mean the carbons to which $R^4$ and $R^5$ are attached, e.g., in formulae (I) and (II) above.

The term "halogen group" as used herein means F, Cl, Br or I.

The term "patient" is used throughout the specification to describe an animal, preferably a human, to whom treatment, including prophylactic treatment, with the compositions according to the present invention is provided. For treatment of those infections, conditions or disease states which are specific for a specific animal such as a human patient, the term patient refers to that specific animal.

The term "neoplasia" is used to describe the pathological process that results in the formation and growth of a neoplasm, i.e., an abnormal tissue that grows by cellular proliferation more rapidly than normal tissue and continues to grow after the stimuli that initated the new growth cease. Neoplasia exhibits partial or complete lack of structural organization and functional coordination with the normal tissue, and usually forms a distinct mass of tissue which may be benign (benign tumor) or malignant (carcinoma). The term "cancer" is used as a general term to describe any of various types of malignant neoplasms, most of which invade surrounding tissues, may metastasize to several sites and are likely to recur after attempted removal and to cause death of the patient unless adequately treated. As used herein, the term cancer is subsumed under the term neoplasia.

The term "virus" shall be used to describe all types of viruses, the growth or replication of which may be inhibited or disease states of which may be treated using one or more methods according to the present invention. Viruses which may be treated according to the present invention include, for example, human immunodeficiency viruses 1 and 2 (HIV-1 and HIV-2), human T-cell leukemia viruses 1 and 2 (HTLV-1 and HTLV-2), respiratory syncytial virus (RSV), human papilloma virus (HPV), adenovirus, hepatitis B virus (HBV), hepatitis C virus (HCV), Epstein-Barr virus (EBV), varicella zoster virus (VZV), cytomegalovirus (CMV), herpes simplex viruses 1 and 2 (HSV-1 and HSV-2), human herpes virus 8 (HHV-8, also known as Kaposi's sarcoma-associated virus) and flaviviruses, including Yellow Fever virus, Dengue virus, Japanese Encephalitis and West Nile viruses, among numerous others.

The term "human immunodeficiency virus" shall be used to describe human immunodeficiency virus (HIV) and its infections, which term shall be used to embrace both human immunodeficieny virus 1 (HIV-1) and human immunodeficiency virus 2 (HIV-2).

The term "human T-cell leukemia virus" shall be used to describe human T-cell leukemia virus and its infections, which term shall be used to embrace both human T-cell leukemia virus 1 (HTLV-1) and human T-cell leukemia virus 2 (HTLV-2).

The term "Hepatitis B Virus (HBV)" is used to describe the virus (serum hepatitis virus) which produces viral hepatitis type B in humans. This is a viral disease with a long incubation period (about 50 to 160 days) in contrast to Hepatitis A virus (infectious hepatitis virus) which has a short incubation period. The virus is usually transmitted by injection of infected blood or blood derivatives or merely by use of contaminated needles, lancets or other instruments. Clinically and pathologically, the disease is similar to viral hepatitis type A; however, there is no cross-protective immunity. Viral antigen (HBAg) is found in the serum after infection.

The term "Hepatitis C Virus (HCV)" is used throughout the specification to describe the hepatitis virus which is the causative agent of non-A, non-B hepatitis. The disease in the acute stage is, in general, milder than hepatitis B, but a greater proportion of such infections become chronic.

The term "Epstein-Barr virus (EBV)" is used throughout the specification to describe a herpetovirus found in cell cultures of Burkitts lymphoma. EBV is the causative agent in infectious mononucleosis, as well as in a number of other related conditions/disease states, including EBV-associated lymphomas.

The term "Varicella-Zoster virus (VZV)" is used to describe Herpes virus varicellae, also known as chicken pox or herpes zoster. Varicella results from a primary infection with the virus; herpes zoster results from secondary invasion by the same or by reactivation of infection which in many instances may have been latent for a number of years. Both the primary and secondary infections of VZV may be treated using compositions according to the present invention.

The term "respiratory syncytial virus (RSV)" is used throughout the specification to describe an RNA-containing virus of the genus *Pneumovirus* that causes minor respiratory infection with rhinitis and cough in adults, but is capable of causing bronchitis and bronchopneumonia in young children. The virus is named for the tendency to form syncytia in tissue culture.

The term "adenovirus" is used throughout the specification to describe a virus of the family adenoviridae which are double-stranded DNA-containing viruses, which infect mammals and birds. The virion is 70 to 90 nm in diameter and is naked (has no envelope). The virus develops in nuclei of infected cells; isolation requires tissue cultures since laboratory animals are not susceptible to apparent infection. The family includes two genera, *Mastadenovirus* and *Acviadenovirus*.

The term "Human Herpes Virus 8 (HHV-8)" is used throughout the specification to describe a herpetovirus which is believed to be the causative agent of Kaposis sarcoma in AIDS patients.

The term "Human Papilloma Virus (HPV)" is used throughout the specification to describe a virus which causes genital warts. Also known as infectious warts virus, HPV is a universal, common, often recurrent viral infection with a large number of serotypes. HPV infection can lead to the formation of genital warts which can, in turn, lead to genital and/or cervical cancer. Genital warts caused by HPV types 1, 2, 6, 11, 16 and 18 are generally transmitted sexually and are often associated with cervical and/or genital cancer. HPV may mature to produce a papillary tumor or wart, which is a circumscribed benign epithelial tumor projecting from the surrounding surface. It is generally a benign epithelial neoplasm consisting of villous or arborescent outgrowths of fibrovascular stroma covered by neoplastic cells.

The term "flavivirus" is used throughout the specification to describe viruses belonging to the genus *Flavivirus* of the family Togaviridae. According to virus taxonomy, about 50 viruses including Hepatitis C virus (HCV), Yellow Fever virus, Dengue Virus, Japanese Encephalitis virus, West Nile virus and related flaviviruses are members of this genus. The viruses belonging to the genus *Flavivirus* are simply called flaviviruses. These viruses were formerly classified as group B arboviruses. The flaviviruses are agents of infectious disease and predominate in East, Southeast and South Asia and Africa, although they may be found in other parts of the world as well.

The term "Yellow Fever virus" is used to describe the flavivirus which is the causative agent of yellow fever. Yellow fever is a tropical mosquito-borne viral hepatitis, due to Yellow Fever virus (YFV), with an urban form transmitted by *Aedes aegypti*, and a rural, jungle or sylvatic form from tree-dwelling mammals by various mosquitos of the *Haemagogus* species complex. Yellow fever is characterized clinically by fever, slow pulse, albuminuria, jaundice, congesion of the face and hemorrhages, especially hematemesis (black vomit). It is fatal in about 5–10% of the cases.

The term "Dengue virus" is used throughout the specification to descibe the flavivirus which is the causative agent(s) of dengue fever/dengue hemorrhagic fever. Dengue is a disease of tropical and subtropical regions occurring epidemically and caused by Dengue virus, one of a group of arboviruses which causes the hemorrhagic fever syndrome. Four grades of severity are recognized: grade I: fever and constitutional symptoms, grade II: grade I plus spontaneous bleeding (of skin, gums or gastrointestinal tract), grade III: grade II plus agitation and circulatory failure and grade IV: profound shock. The disease is transmitted by a mosquito of the genus *Aedes* (generally *A. aegyptil*, but frequently, *A. albopictus*). Also called Aden, bouquet, breakbone, dandy, date, dengue (hemorrhagic) or polka, solar fever, stiffneck fever, scarlatina rheumatica or exanthesis arthorosia. Hemorrhagic dengue is a more pathogenic epidemic form of dengue which has erupted in a number of epidemic outbreaks in the Pacific region in recent years.

The term "*Mycobacterium* spp." refers to a genus of aerobic, nonmotile bacteria containing Gram-positive, acidfast, slender, straight or slightly curbed rods. A number of *Mycobacterium* associated diseases are associated with immunocompromised patients, especially those with AIDS. *Mycobacterium tuberculosis* refers to the causative agent of tuberculosis, which may affect any tissue or organ of the body, the most common location of the disease being found in the lungs. The present invention also relates to the treatment of tuberculosis in patients in need of therapy.

The term "West Nile virus" is used to describe the flavivirus which is the causative agent of West Nile fever, a disease characterized by headache, fever, masculopapular rash, myalgia, lymphadenopathy and leukopenia. The virus is spread by *Culex* mosquitoes from a reservoir in birds. Although in the past, West Nile virus infections had been considered virtually nonexistent in the United States, recent developments have suggested that West Nile and other flavivirus infections will appear with greater regulatory in the future in the United States.

The term "pharmaceutically acceptable salt" is used throughout the specification to describe a salt form of one or more of the compositions (and in particularly preferred aspects according to the present invention, phosphate salts) herein which are presented to increase the solubility of the compound in saline for parenteral delivery or in the gastric juices of the patient's gastrointestinal tract in order to promote dissolution and the bioavailability of the compounds. Pharmaceutically acceptable salts include those derived from pharmaceutically acceptable inorganic or organic bases and acids. Suitable salts include those derived from alkali metals such as potassium and sodium, alkaline earth metals such as calcium, magnesium and ammonium salts, among numerous other acids well known in the pharmaceutical art. Sodium and potassium salts are particularly preferred as neutralization salts of carboxylic acids and free acid phosphate containing compositions according to the present invention. The term "salt" shall mean any salt consistent with the use of the compounds according to the present invention. In the case where the compounds are used in pharmaceutical indications, including the treatment of neoplasia, including cancer, the term "salt" shall mean a pharmaceutically acceptable salt, consistent with the use of the compounds as pharmaceutical agents.

The term "inhibitory effective concentration" or "inhibitory effective amount" is used throughout the specification to describe concentrations or amounts of compounds according to the present invention which substantially or significantly inhibit the growth or replication of susceptible viruses, especially including human immunodeficiency viruses 1 and 2 (HIV-1 and HIV-2), human T-cell leukemia viruses 1 and 2 (HTLV-1 and HTLV-2), respiratory syncytial virus (RSV), human papilloma virus (HPV), adenovirus, hepatitis B virus (HBV), hepatitis C virus (HCV), Epstein-Barr virus (EBV), varicella zoster virus (VZV), cytomegalovirus (CMV), herpes simplex viruses 1 and 2 (HSV-1 and HSV-2), human herpes virus 8 (HHV-8, also known as Kaposi's sarcoma-associated virus) and flaviviruses, including Yellow Fever virus, Dengue virus, Japanese Encephalitis and West Nile viruses, among numerous others.

The terms "an effective amount", "therapeutic effective amount", or "therapeutically effective amount" shall mean an amount or concentration of a compound according to the present invention which is effective within the context of its administration or use, including, for example, the treatment or prevention of viral infections. Thus, the term "effective amount" is used throughout the specification to describe concentrations or amounts of compounds according to the present invention which may be used to produce a favorable change in the disease or condition treated, whether that change is a remission, a decrease in growth or size of cancer or a tumor, a favorable physiological result, a reduction in the growth or elaboration of a microbe, or the like, depending upon the disease or condition treated.

The term "preventing effective amount" is used throughout the specification to describe concentrations or amounts of compounds according to the present invention which are prophylactically effective in preventing, reducing the likelihood of infection or delaying the onset of infections in patients caused by human immunodeficiency viruses 1 and 2 (HIV-1 and HIV-2), human T-cell leukemia viruses 1 and 2 (HTLV-1 and HTLV-2), respiratory syncytial virus (RSV), human papilloma virus (HPV), adenovirus, hepatitis B virus (HBV), hepatitis C virus (HCV), Epstein-Barr virus (EBV), varicella zoster virus (VZV), cytomegalovirus (CMV), herpes simplex viruses 1 and 2 (HSV-1 and HSV-2), human herpes virus 8 (HHV-8, also known as Kaposi's sarcoma-associated virus) and flaviviruses, including Yellow Fever virus, Dengue virus, Japanese Encephalitis and West Nile viruses, among numerous others.

The term "coadministration" or "combination therapy" is used to describe a therapy in which at least two active compounds in effective amounts are used to treat a viral or fungal infection at the same time. Although the term coadministration preferably includes the administration of two active compounds to the patient at the same time, it is not necessary that the compounds be administered to the patient at the same time, although effective amounts of the individual compounds will be present in the patient at the same time.

The term "organic solvent" includes but not is limited to 1,2-dichloroethane, dimethoxyethane, diethylene glycol dimethyl ether, tetrahydrofuran, dioxane or diisopropyl ether, hydrocarbons such as hexane, heptane, cyclohexane, toluene or xylene, alcohols such as methanol, ethanol, 1-propanol, 2-propanol, 1-butanol, 2-butanol, tert-butanol or ethylene glycol, ketones such as methyl ethyl ketone or isobutyl methyl ketone, amides such as dimethylformamide, dimethylacetamide or N-methylpyrrolidone, dimethoxyethane, tetrahydrofuran, dioxane, cyclohexane, toluene, xylene, alcohols, e.g. ethanol, 1-propanol, 2-propanol, 1-butanol, tert-butanol and mixtures thereof. 1,2-Dichloroethane is a preferred organic solvent.

"Lewis acids" include but are not limited to trimethylsilyl trifluoromethanesulfonate (TMSOTf), titanium chloride, tin chloride, zinc chloride, zinc bromide, zinc iodide, magnesium chloride, titanium alkoxide, boron bromide, boron chloride, boron fluoride, boron trifluoride-diethyl ether complex, aluminum chloride, aluminum bromide, thionyl chloride, phosphorus oxychloride, phosphorus chloride, trimethylsilyl chloride, and trimethylsilyl iodide. TMSOTf is a preferred Lewis acid.

Compounds according to the present invention may be used in pharmaceutical compositions having biological/pharmacological activity for the treatment of, for example, neoplasia, including cancer, as well as a number of other conditions and/or disease states, as intermediates in the synthesis of compounds exhibiting biological activity as well as standards for determining the biological activity of the present compounds as well as other biologically active compounds. In some applications, the present compounds may be used for treating microbial infections, especially including viral infections. These compositions comprise an effective amount of any one or more of the compounds disclosed hereinabove, optionally in combination with a pharmaceutically acceptable additive, carrier or excipient.

A further aspect of the present invention relates to the treatment of neoplasia, including cancer, comprising administering to a patient in need thereof an effective amount of a compound as described hereinabove, optionally in combination with a pharmaceutically acceptable additive, carrier or excipient. The present invention also relates to methods for inhibiting the growth of neoplasia, including a malignant tumor or cancer comprising exposing the neoplasia to an inhibitory or therapeutically effective amount or concentration of at least one of the disclosed compounds. This method may be used therapeutically, in the treatment of neoplasia, including cancer or in comparison tests such as assays for determining the activities of related analogs as well as for determining the susceptibility of a patient's cancer to one or more of the compounds according to the present invention. Primary utility resides in the treatment of neoplasia, including cancer, especially including lung cancer, breast cancer and prostate cancer, among others.

A preferred therapeutic aspect according to the present invention relates to methods for treating neoplasia, including benign and malignant tumors and cancer in animal or human patients, and in preferred embodiments, cancers which have developed drug resistance, including, for example, multiple drug resistant breast cancer comprising administering therapeutically effective amounts or concentrations of one or more of the compounds according to the present invention to inhibit the growth or spread of or to actually shrink the neoplasm in the animal or human patient being treated.

Cancers which may be treated using compositions according to the present invention include, for example, stomach, colon, rectal, liver, pancreatic, lung, breast, cervix uteri, corpus uteri, ovary, prostate, testis, bladder, renal, brain/cns, head and neck, throat, Hodgkins disease, non-Hodgkins leukemia, multiple myeloma leukemias, skin melanoma, acute lymphocytic leukemia, acute mylogenous leukemia, Ewings Sarcoma, small cell lung cancer, choriocarcinoma, rhabdomyosarcoma, Wilms Tumor, neuroblastoma, hairy cell leukemia, mouth/pharynx, oesophagus, larynx, melanoma, kidney and lymphoma, among others. Compounds according to the present invention are particularly useful in the treatment of lung cancer, breast cancer and prostate cancer.

In the present methods, in certain preferred embodiments, it has been found advantageous to coadminister at least one additional anti-neoplastia agent for the treatment of neoplasia, including cancer. In these aspects according to the present invention, an effective amount of one or more of the compounds according to the present invention is co-administered along with an effective amount of at least one additional antineoplastia/anticancer agent such as, for example cyclophosphamide.

The compositions of the present invention may be formulated in a conventional manner using one or more pharmaceutically acceptable carriers. Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as prolamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally, or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

The pharmaceutical compositions of this invention may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of novel nucleoside of the instant invention that may be combined with the carrier materials to produce a single dosage form will vary depending upon the host treated, the particular mode of administration. Preferably, the compositions should be formulated so that a dosage of between about 20 and 80 mg/m$^2$/day of the novel nucleoside can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease or condition being treated.

Chemistry

The novel compounds of the instant invention were generally prepared in the following manner.

Referring to FIG. 1, Scheme 1, halogen-substituted 4-aminopyridines useful as intermediates in making the novel nucleosides of the instant invention were synthesized as follows. Treatment of commercially available 3-chlorotetrafluoropyridine (1) and 3,5-dichlorotrifluoropyridine (4) with ammonium hydroxide at room temperature gave almost quantitatively 4-amino-3-chloro-2,5,6-trifluoropyridine (2) and 4-amino-3,5-dichloro-2,6-difluoropyridine (5), respectively. Chambers, R. D.; Hutchinson, J.; Musgrave, W. K. R. *J. Chem. Soc.* 1964, 5634–5640. Catalytic hydrogenation of 2 afforded 4-amino-2,3,6-trifluoropyridine (3) in high yield. Catalytic hydrogenation of 5 was reported to give 4-amino-2,6-difluoropyridine (7); McNamara, D. J.; Cook, P. D. *J. Med. Chem.* 1987 30, 340–347; however, when the reaction was stopped at an early stage, a mixture of 4-amino-3-chloro-2,6-difluoropyridine (6) and 7 were produced, which was easily separated by flash silica gel column chromatography.

2-Chloro-5-fluoropyridine (9), a highly volatile substance, was synthesized from thermolysis of 2-chloro-5-pyridinediazonium tetrafluoroborate (8). Hand, E. S.; Baker, D. C. *Synthesis* 1989, 905–908. The isolation of 9 by the literature procedure was very complicated, in that it included repeated extractions, repeated distillations, treatment with sulfuric acid and sodium hydroxide, and steam distillation. In our hands, the reported yield of 70% was difficult to obtain after these operations. To improve upon these complicated procedures, following the thermolysis of compound 8, the reaction mixture was directly treated with 50% hydrogen peroxide and trifluoroacetic acid to give 2-chloro-5-fluoropyridine-N-oxide (10), which was easily isolated, with a total yield of 73%. Nitration of 10, followed by catalytic hydrogenation of the resulting 2-chloro-5-fluoro-4-nitropyridine-1-oxide (11) removed the N-oxide function, as well as reduced the nitro group to give the desired 4-amino-2-chloro-5-fluoropyridine (12). N-Oxidation of commercially available 2,5-dichloropyridine (13), followed by nitration and reduction yielded 4-amino-2,5-dichloropyridine (16).

Figure 2:
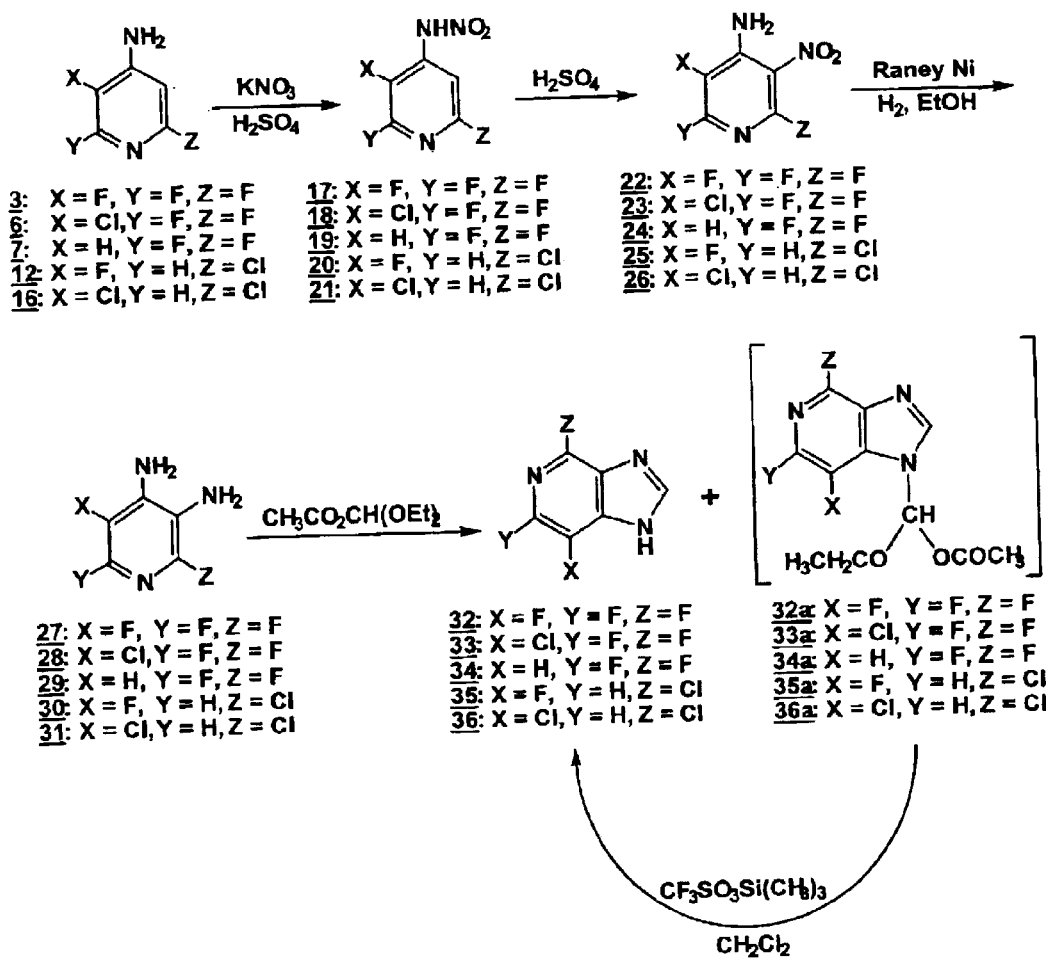
FIG. 2 illustrates the synthesis of various halogen-substituted imidazo[4,5c]pyridines useful as intermediates in making novel nucleosides of the instant invention.

Various halogen-substituted imidazo[4,5-c]pyridines (32–36) were synthesized from the corresponding halogen-substituted 4-pyridinamines for the synthesis of 4,6-dichloroimidazo[4,5-c]pyridine, in accordance with Scheme 2 illustrated in FIG. 2. This scheme is a variation of that used in Rousseau, R. J.; Robins, R. J. *J. Heterocycl. Chem.* 1965 2, 196–201. Nitration of compounds 3, 6, 7, 12 and 16 with potassium nitrate in sulfuric acid gave the respective 4-nitraminopyridines (17–21). Rearrangement of compounds 17–21 in concentrated sulfuric acid produced the respective 4-amino-3-nitropyridine derivatives 22–26. Catalytic hydrogenation of 22–26 in the presence of Raney nickel afforded the corresponding 3,4-diaminopyridine derivatives 27–31. Ring closure of compounds 27–31 by reaction with diethoxymethyl acetate gave the desired halogen-substituted imidazo[4,5c]pyridines 32–36, Kroon, C.; van den Brink, A. M.; Vlietstra, E. J.; Salemink, C. A. *Rec. Trav. Chim.* 1976 95, 127–156 and N-1 substituted compounds 32a–36a which were separated by silica gel column chromatography; these by-products were easily converted back to compounds 32–36 by reaction with trimethylsilyl trifluoromethanesulfonate. The synthesis of 4,6-difluoroimidazo[4,5-c]pyridine (34) has been previous reported by a different synthetic route; however, this method was rather lengthy and the overall yield was quite low. Kroon, C.; van den Brink, A. M.; Vlietstra, E. J.; Salemink, C. A. *Rec. Trav. Chim.* 1976 95, 127–156.

Figure 3:
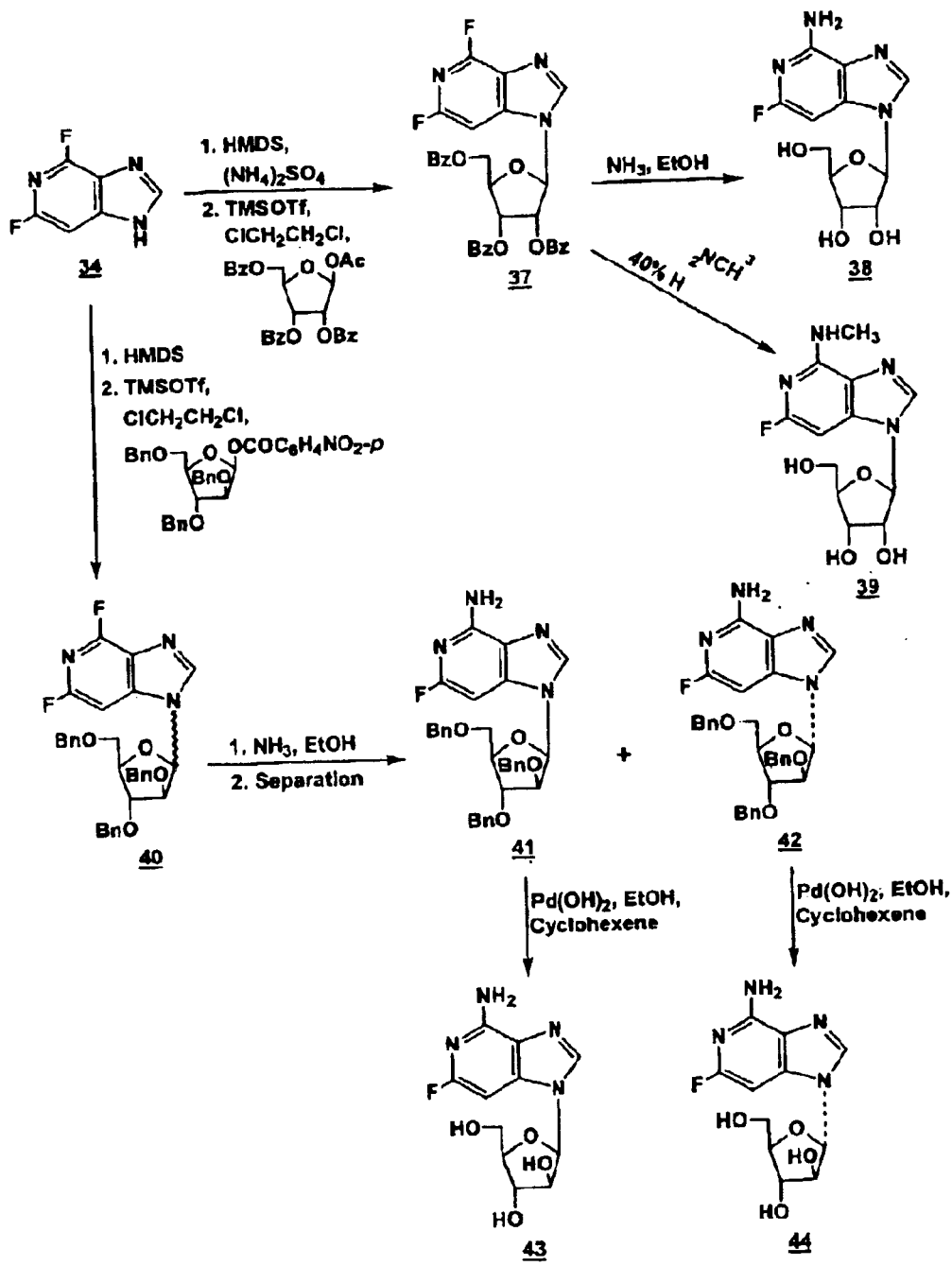
FIG. 3 illustrates the synthesis of the novel nucleosides 4-Amino-6-fluoro-1-(β-D-ribofuranosyl)imidazo[4,5-c] pyridine; 6-Fluoro-4-methylamino-1-(β-D-ribofuranosyl) imidazo[4,5-c]pyridine; 4-Amino-6-fluoro-1-β-D-arabinofilranosylimidazo[4,5-c]pyridine; and 4-Amino-6-fluoro-1-α-D-arabinofuranosylimidazo[4,5-c]pyridine.

Treatment of 4,6-difluoroimidazo[4,5-c]pyridine (34) with excess hexamethyldisilazane and a catalytic amount of ammonium sulfate gave the trimethylsilyl derivative, which was treated with 1-O-acetyl-2,3,5-tri-O-benzoyl-β-D-ribofuranose in 1,2-dichloroethane using trimethylsilyl trifluoromethanesulfonate (TMSOTf) as a catalyst at room temperature to give the tribenzoyl-protected nucleoside derivative 37 as illustrated in Scheme 3 shown in FIG. 3. Treatment of 37 with either saturated ethanolic ammonia or 40% methylamine removed the protecting groups and displaced the 4-fluoro group in one step to produce the respective target nucleosides 38 and 39. Refluxing of silylated 34 with 2,3,5-tri-O-benzyl-1-O-(4-nitro-benzoyl)-D-arabinofuranose in 1,2-dichloroethane in the presence of TMSOTf under nitrogen afforded a mixture of α- and β-nucleosides 40. Treatment of 40 with ammonia saturated ethanol gave the 4-amino-6-fluoro-1-(2,3,5-tri-O-benzyl-β-D-arabinofuranosyl)imidazo[4,5-c]pyridine (41) and its a analogue 42, which were separated by silica gel chromatography. Debenzylation of 41 and 42 with palladium (II) oxide hydrate and cyclohexene in ethanol afforded the target compound 43 and its α analogue 44.

The assignment of the anomeric configurations of these nucleosides (41–44) was made on the basis of the characteristics of the proton NMR spectra in Table 1. The 4'-H protons of the α anomers appear at a lower field than those of the β anomers. Conversely, the 5'-H protons of the α-anomers appear at a higher field than those of the β-anomers. These shifts are attributed to the fact that protons at the syn-position relative to the base are more deshielded than those in the anti-position relative to the base. The 4'-H protons of the α-anomers and the bases are on the same side of the sugar ring and those of β-anomers are on the opposite side. In contrast, the 5'-H protons of the α-anomers and the bases are on the opposite side of the sugar ring and those of β-anomers are on the same side. The findings are consistent with reports by others with both pyrimidine and purine nucleosides. Okabe, M.; Sun, R. C.; Tam, S. Y. K; Todaro, L. J.; Coffen, D. L. *J. Org. Chem.,* 1988 53, 4780–4786. Chu, C. K.; Ullas, G. V.; Jeong, L. S.; Ahn, S. K.; Doboszewski, B.; Lin, Z. X.; Beach, J. W.; Schinazi, R. F. *J. Med. Chem.* 1990 33, 1553–1561.
Tiwari, K. N.; Montgomery, J. A.; Secrist, J. A., III *Nucleosides & Nucleotides* 1993 12, 841–846.

TABLE 1

| | Proton NMR chemical shifts δ (ppm) | | | |
|---|---|---|---|---|
| Compd | 4'-H[a] | Δδ | 5'-H[a] | Δδ |
| 41 (β)[b] | 4.10 (anti) | 0.15 | 3.70 (syn) | 0.12 |
| 42 (α)[b] | 4.25 (syn) | | 3.58 (anti) | |
| 43 (β)[c] | 3.73 (anti) | 0.29 | 3.65 (syn) | 0.13 |
| 44 (α)[c] | 4.02 (syn) | | 3.52 (anti) | |

[a]Stereochemistry relative to the base.
[b]Spectra were recorded in CDCl$_3$;
[c]in DMSO-d$_6$.

Figure 4:
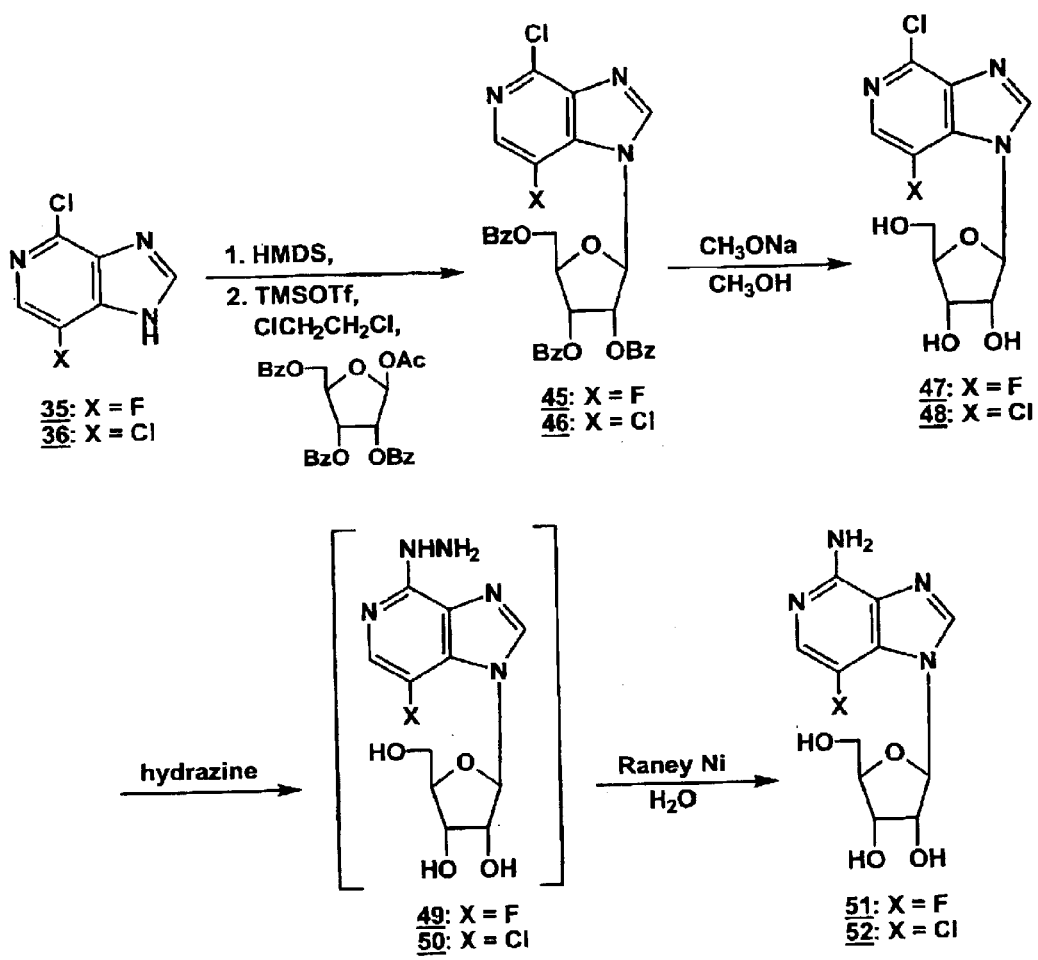
FIG. 4 illustrates the synthesis of the novel nucleosides 4-Amino-7-fluoro-1-(β-D-ribofuranosyl)imidazo[4,5-c] pyridine and 4-Amino-7-chloro-1-(β-D-ribofuranosyl) imidazo[4,5-c]pyridine.

The synthesis of 3-halogen-substituted 3-deazaadenosine analogues 51 and 52 is shown in Scheme 4 illustrated in FIG. 4. Condensation of silylated 4-chloro-7-fluoroimidazo[4,5-c]pyridine (35) and silylated 4,7-dichloroimidazo[4,5-c] pyridine (36) with 1-O-acetyl-2,3,5-tri-O-benzoyl-β-D-ribofuranose in 1,2-dichloroethane in the presence of TMSOTf gave the 3-deaza-3-halogen-substituted purine nucleosides 45 and 46, respectively. Deblocking of 45 and 46 with sodium methoxide in methanol yielded the corresponding nucleoside derivatives 47 and 48. Attempts at conversion of the 4-chloro substituents on 45 and 46 to the corresponding amino functions by either ammonia saturated ethanol or liquid ammonia at various temperatures were unsuccessful and resulted in either a decomposed by-product or recovery of the starting material. However, treatment of 47 and 48 with anhydrous hydrazine, Secrist, J. A., III; Comber, R. N.; Gray, R. J.; Gilroy, R. B.; Montgomery, J. A. *J. Med. Chem.* 1993 36, 2102–2106, followed by catalytic hydrogenation of compounds 49 and 50 with Raney nickel furnished 51 and 52.

Figure 5:
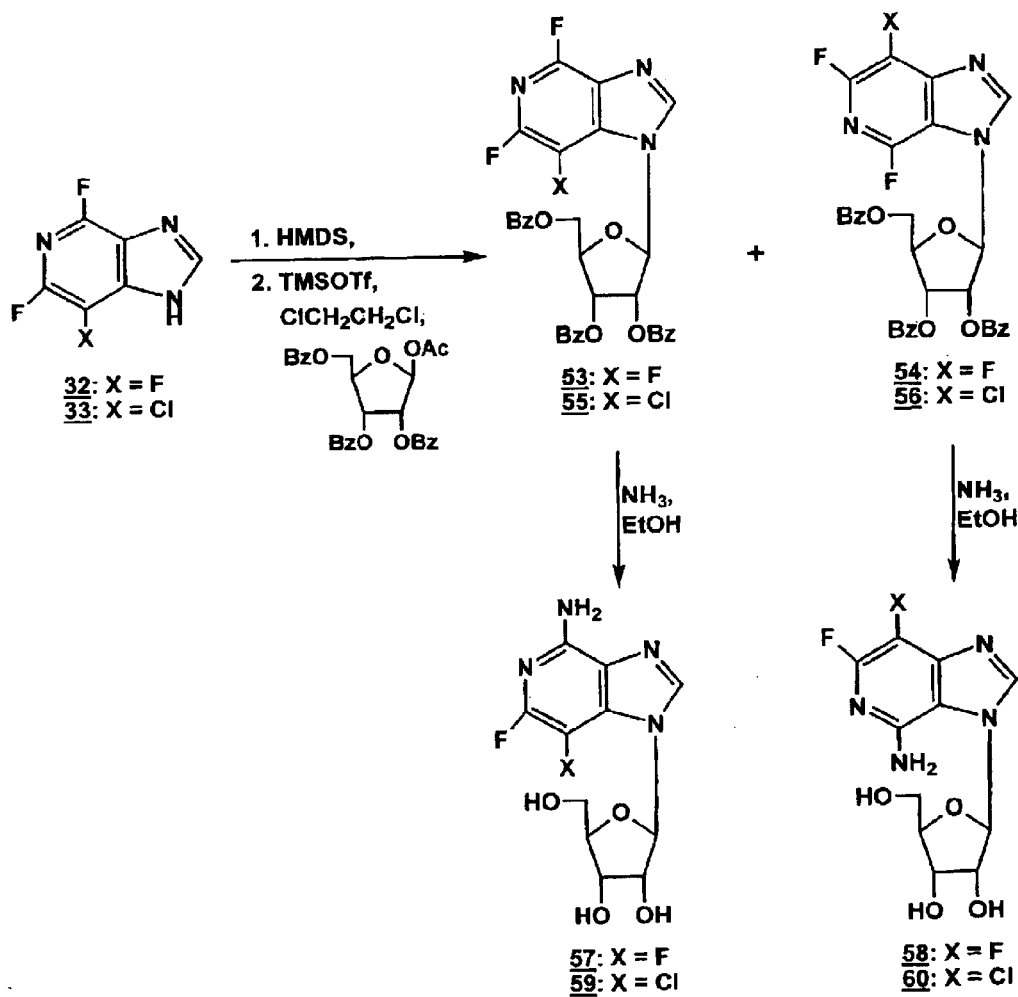
FIG. 5 illustrates the synthesis of the novel nucleosides 4-Amino-6,7-difluoro-1-(β-D-ribofuranosyl)imidazo[4,5-c] pyridine; 4-Amino-6,7-difluoro-3-(β-D-ribofuranosyl) imidazo[4,5-c]pyridine; 4-Amino-7-chloro-6-fluoro-1-(β-D-ribofuranosyl)imidazo[4,5-c]pyridine; and 4-Amino-7-chloro-6-fluoro-3-(β-D-ribofuranosyl)imidazo[4,5-c] pyridine.

The synthesis of 2,3-dihalogen-substituted 3-deazaadenosine analogues 57–60 is depicted in Scheme 5 shown in FIG. 5. Condensation of silylated 4,6,7-trifluoroimidazo[4,5-c]pyridine (32) and silylated 7-chloro-4,6-difluoroimidazo[4,5-c]pyridine (33) with 1-O-acetyl-2,3,5-tri-O-benzoyl-β-D-ribofuranose in 1,2-dichloroethane in the presence of TMSOTf gave the corresponding protected 1-ribosides 53 and 55, and 3-ribosides 54 and 56. Treatment of compounds 53–56, with ammonia saturated ethanol afforded the respective target compounds 57–60. The assignment of the N-glycosidic linkage of the N$^1$- and N$^3$-isomers of compounds 57–60 was based upon the UV spectra of these derivatives. The UV spectra of the N$^1$-3-deazapurine nucleoside isomers showed a maximum peak at 274 nm (57 and 59), while the N$^3$-isomers showed a maximum peak at 292 nm (58 and 60). Furthermore, the NMR spectra of the 2-H protons of the N$^3$-isomers were downfield from those of the corresponding N$^1$-isomers. For example, the chemical shifts of the 2-H protons of the N$^3$-isomers 58 and 60 appeared at 8.54 and 8.55 ppm and for the N$^1$-isomers 57 and 59 at 8.43 and 8.51 ppm, respectively. These results are similar to those obtained with other 3-deazapurine nucleosides. Montgomery, J. A.; Shortnacy, A. T.; Clayton, S. D. *J. Heterocycl. Chem.* 1977 14, 195–197. Poonian, M. S.; McComas, W. W. *J. Med. Chem.* 1979 22, 958–962.

Figure 6:
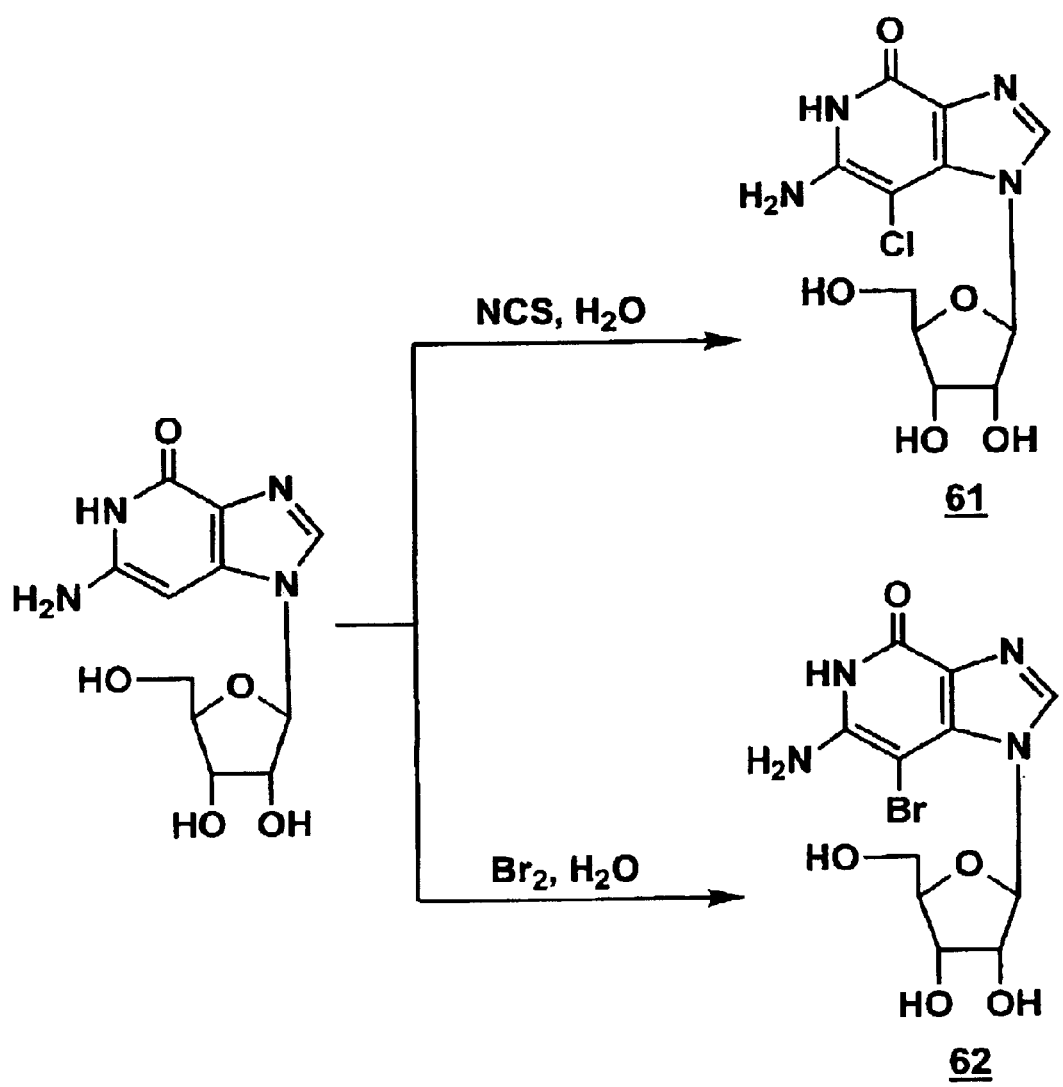
FIG. 6 illustrates the synthesis of the novel nucleosides 6-Amino-7-chloro-1,5-dihydro-1-β-D-ribofuranosylimidazo

The synthesis of 3-deaza-3-halogen-substituted 3-deazaguanosine analogues is illustrated in Scheme 6 shown in FIG. 6. Halogenation of 3-deazaguanosine, which was synthesized by a known procedure with N-chlorosuccinimide in water and bromine-water, respectively, gave the corresponding 3-deaza-3-chloroguanosine (61) and 3-deaza-3-bromoguanosine (62). Revankar, G. R.; Gupta, P. K.; Adams, A. D.; Dalley, N. K.; McKernan, P. A.; Cook, P. D.; Canonico, P. G.; Robins, R.

K. *J. Med. Chem.*, 1984 27, 1389–1396; Cook, P. D.; Rousseau, R. J.; Mian, A. M.; Dea, P.; Meyer, R. B., Jr.; Robins, R. K. *J. Amer. Chem. Soc.* 1976 98, 1492–1498.

Biology

The synthesized compounds were evaluated in vitro for their cytotoxicity against the L1210 and P388 leukemias, the CCRF-CEM lymphoblastic leukemia, and the $B_{16}F_{10}$ melanoma cell lines and the results are shown in Table 2. Among these compounds, 3-deaza-3-chloroguanosine (61) showed activity with $IC_{50}$ values of 12, 40, 30 and 35 $\mu M$ and 3-deaza-3-bromoguanosine (62) produced $IC_{50}$ values of 3, 7, 9 and 7 $\mu M$ against L1210, P388, CCRF-CEM and $B_{16}F_{10}$ cells, respectively. The halogen-substituted 3-deazaadenosine derivatives 38, 51, 57 and 59 showed moderate to weak activities, and the other compounds had only slight or no activity in concentrations up to 100 $\mu M$ against these neoplastic cell lines.

Antiviral assays were performed against hepatitis B virus (HBV) and human immunodeficiency virus (HIV-IIIB) in vitro as previously described. Lin, T. S.; Luo, M. Z.; Liu, M. C.; Pai, S. B.; Dutschman, G. E.; Cheng, Y. C., *J. Med. Chem.* 1994 37, 798–803. Among these compounds, 3-deaza-3-chloro-2-fluoroadenosine (59), 3-deaza-3-fluoroadenosine (51) and 4-amino-6,7-difluoro-3-(β-D-ribfuranosyl)imidazo[4,5c]pyridine (58) showed moderate activity against HBV with $EC_{50}$ values of 7.5, 9.2 and 10 $\mu M$, respectively. The remaining compounds showed little or no activity against HBV and HIV-IIIB up to their maximum tested concentrations of 10 and 100 $\mu M$, respectively.

TABLE 2

Evaluation of the cytotoxicity of halogen-substituted 3-deazaadenosine and 3-deazaguanosine analogues against L1210, P388, CCRF-CEM, and $B_{16}F_{10}$ cell lines in vitro

| Compd | L1210 | P388 | CCRF-CEM | $B_{16}F_{10}$ |
|---|---|---|---|---|
| | | $IC_{50}$ $(\mu M)^a$ | | |
| 38 | 35 | 50 | 100 | 40 |
| 39 | >100 | >100 | 100 | >100 |
| 43 | >100 | >100 | >100 | >100 |
| 44 | >100 | >100 | >100 | >100 |
| 51 | 15 | 100 | 60 | 45 |
| 52 | >100 | >100 | >100 | >100 |
| 57 | 90 | 90 | 40 | 100 |
| 58 | >100 | >100 | >100 | >100 |
| 59 | 55 | 90 | 60 | 100 |
| 60 | >100 | >100 | >100 | >100 |
| 61 | 12 | 40 | 30 | 35 |
| 62 | 3 | 7 | 9 | 7 |

$^a IC_{50}$ values represent the drug concentration ($\mu M$) required to inhibit cancer cell replication by 50%. The compounds were tested up to a concentration of 100 $\mu M$.

The invention is described further in the following examples, which are illustrative only and are in no way limiting.

EXAMPLE 1

The following examples describe syntheses employed in making the compounds of the instant invention in accordance with the aforementioned Schemes 1 through 6 illustrated in FIGS. 1 through 6.

Experimental Section

Melting points for each of the examples described hereinafter were determined with a Thomas-Hoover Unimelt apparatus and are uncorrected. $^1H$ NMR spectra were recorded on a Varian EM-390 (90 MHz) or Gemini-300 (300 MHz) NMR spectrometer with $Me_4Si$ as the internal reference. The UV spectra were recorded on a Beckman-25 spectrophotometer. Mass spectra were recorded on a VG-ZAB-SE mass spectrometer in the fast bombardment (FAB) mode (glycerol matrix). Column chromatography was conducted with Merck silica gel 60, 230–400 mesh. TLC was performed on EM precoated silica gel sheets containing a fluorescent indicator. Elemental analyses were carried out by the Baron Consulting Co., Orange, Conn., USA.

EXAMPLE 2

Scheme 1

4-Amino-3-chloro-2,5,6-trifluoropyridine (2). This compound was prepared by a modification of the procedure of Chambers et al., *J. Chem. Soc.* 1964, 5634–5640. A mixture of 3-chloro-2,4,5,6-tetrafluoropyridine (1, 37.4 g, 201 mmol) and 150 mL of 28% ammonium hydroxide was stirred at room temperature for 5 h. The resulting white crystals were collected and carefully washed with ice water to give 2 as a white solid (35 g). The combined filtrate and washings were extracted with ether. The ether extract was dried ($MgSO_4$), filtered and evaporated in vacuo to give additional 2 (1.3 g); total yield: 26.3 g (99%). The product was used directly for the next step in the reaction. A small sample was purified by silica gel column chromatography: mp 118–120° C. (Lit., Chambers et al., *J. Chem. Soc.* 1964, 5634–5640, mp 117–118° C.).

4-Amino-3,5-dichloro-2,6-difluoropyridine (5). This compound was prepared from 3,5-dichloro-2,4,6-trifluoropyridine (24.5 g) by a procedure similar to that described for compound 2: yield, 23.7 g (98%); mp 110° C. (Lit., Chambers et al., *J. Chem. Soc.* 1964, 5634–5640 mp 112–113° C.).

4-Amino-2,3,6-trifluoropyridine (3). A suspension of 4-amino-3-chloro-2,5,6-trifluoropyridine (2, 19.7 g, 108 mmol), 10% Pd/C (1.8 g) and triethylamine (20 mL, 140 mmol) in 150 mL of anhydrous ethanol was hydrogenated at 50 psi in a Parr hydrogenation apparatus until TLC showed the reaction was completed (about 18 hours). The catalyst was removed by filtration and carefully washed with ethanol. The combined filtrate and washings were evaporated to dryness in vacuo. The residue was stirred with 80 mL of water for 1 h, filtered, and washed with water to give 3 (14 g) as a white solid. The filtrate and washings were combined and extracted with ether. The combined ether layers were then dried ($MgSO_4$) and concentrated to give an additional 1.3 g of 3 (total yield: 15.3 g, 96%). A small analytical sample was purified by silica gel column chromatography ($R_f$ 0.47, $CH_2Cl_2$): mp 94–96° C.; $^1H$ NMR ($CDCl_3$) δ4.78 (br s, 2 H, 4-$NH_2$, $D_2O$ exchangeable), 6.20 (d, 1 H, 5-H). Analysis calculated for $C_5H_3F_3N_2$: C, 40.55; H, 2.04; N, 18.92. Found: C, 40.60; H, 2.16; N, 18.67.

4-Amino-3-chloro-2,6-difluoropyridine (6) and 4-amino-2,6-difluoropyridine (7). A suspension of 19.9 g (100 mmol) of 5, 2.2 g of 10% Pd/C and 27 mL (190 mmol) of triethylamine in 100 mL of anhydrous ethanol was hydrogenated at 50 psi in a Parr hydrogenation apparatus overnight (about 18 h). The catalyst was filtered and carefully washed with ethanol. The combined filtrate and washings were evaporated to dryness in vacuo. The residue was partitioned between ether and water, and the water layer was extracted with ether. The combined ether layers were dried ($MgSO_4$) and concentrated to dryness. The residue was dissolved in ethanol and the solution was treated with 50 g of silica gel. The solvent was removed in vacuo to give a powder, which was purified by silica gel column chromatography, eluted with $CH_2Cl_2$ to afford 9.4 g (57%) of 6 and 4.3 g (33%) of 7.

Compound 6 was isolated as a white solid: mp 84–85° C.; TLC, $R_f$ 0.55 ($CH_2Cl_2$); $^1H$ NMR ($CDCl_3$) δ5.15 (br s, 2 H, NH$_2$, D$_2$O exchangeable), 6.20 (s, 1 H, 5-H). Analysis calculated for C$_5$H$_3$ClF$_2$N$_2$: C, 36.49; H, 1.84; N, 17.02. Found: C, 36.78; H, 2.09; N, 16.89.

Compound 7 was isolated as a white solid: mp 126–128° C. (Lit., Secrist, et al., *J. Med. Chem.* 1988 31, 405–410 mp 125–127° C.); TLC, R$_f$0.37 (CH$_2$Cl$_2$); $^1$H NMR (DMSO-d$_6$) δ6.00 (s, 2 H, 3- and 5-H), 6.70 (br s, 2 H, NH$_2$, D$_2$O exchangeable). Analysis calculated for C$_5$H$_4$F$_2$N$_2$: C, 46.16; H, 3.10; N, 21.54. Found: C, 46.01; H, 3.39; N, 21.29.

2-Chloro-5-fluoropyridine-1-oxide (10). Hand, E. S.; Baker, D. C. *Synthesis* 1989, 905–908. A suspension of 2-chloro-5-pyridinediazonium tetrafluoroborate (8, 7.6 g, 33.4 mmol) in dry heptane (50 mL) was heated to 105° C. (oil bath temperature) for 2 h. A rapid evolution of nitrogen was observed after 10–15 min, which lasted for about 30 min. The reaction mixture formed two layers: the clear upper heptane layer and the blackened dark lower layer. The temperature was then lowered to 70° C., and 100 mL of trifluoroacetic acid and 11 mL of 50% hydrogen peroxide were subsequently added from the top of the condenser. The reaction mixture was stirred at 70–75° C. until TLC showed that the reaction was complete (around 20 hours). The lower dark layer gradually changed to a clear orange solution during the reaction process. The two-layer mixture was evaporated to dryness in vacuo and co-evaporated with toluene (50 mL). To the residue were added 20 mL of water and 100 mL of methylene chloride, and the mixture was neutralized by dropwise addition of 28% ammonium hydroxide solution with stirring. The aqueous layer was further extracted with methylene chloride and the combined organic layer was dried, filtered and evaporated to give the crude product, which was purified by silica gel column chromatography (CH$_2$Cl$_2$/EtOAc, 1:1, v/v, R$_f$0.23) to give 3.6 g (73%) of product as a white solid: mp 98–100° C.; $^1$H NMR (CDCl$_3$) δ7.15 (m, 1 H, 3-H), 7.60 (m, 1H, 4-H), 8.40 (dd, 1 H, 6-H, J=2.0 Hz, 8.5 Hz). Analysis calculated for C$_5$H$_3$ClFNO.0.5 H$_2$O: C, 38.36; H, 2.56; N, 8.95. Found: C, 38.13; H, 2.19; N, 8.65.

2-Chloro-5-fluoro-4-nitropyridine-1-oxide (11). 2-Chloro-5-fluoropyridine-N-oxide (10, 3.5 g, 23.7 mmol) was gradually added to 46 mL of concentrated sulfuric acid, followed by 10 g of potassium nitrate with stirring. The reaction mixture was heated at 120° C. for 2 h, cooled and poured onto 160 g of crushed ice. The solution was neutralized by dropwise addition of 28% ammonium hydroxide with stirring, while the temperature was maintained below 15° C. with an ice bath. The light yellow crystals which precipitated were collected by filtration, washed with ice water, and dried to yield 2.7 g (59%) of product. A small sample was purified by silica gel column chromatography (CH$_2$Cl$_2$/EtOAc, 4:1, v/v, R$_f$ 0.71): mp 131–132° C.; $^1$H NMR (DMSO-d$_6$) δ8.70 (m, 1 H, 3-H), 9.12 (m, 1 H, 6-H). Analysis calculated for C$_5$H$_2$ClFN$_2$O$_3$: C, 31.19; H, 1.05; N, 14.55. Found: C, 31.36; H, 1.16; N, 14.75.

4-Amino-2-chloro-5-fluoropyridine (12). A mixture of 2-chloro-5-fluoro-4-nitropyridine-1-oxide (11, 1.3 g, 6.8 mmol) and 1.6 g of Raney nickel in 80 mL of anhydrous ethyl alcohol was hydrogenated at 40 psi in a Parr hydrogenation apparatus for 3 h when TLC showed that the starting material had disappeared and a new spot was detected (CH$_2$Cl$_2$/EtOAc, 4:1, v/v, R$_f$0.78 and 0.71, for the starting material and the product, respectively). The catalyst was removed by filtration and washed carefully with ethyl alcohol. The filtrate and washings were combined and evaporated in vacuo to give 0.9 g (91%) of product as an off-white solid. A small analytical sample was purified by recrystallization from hot water to afford white crystals: mp 110–111° C.; $^1$H NMR (CDCl$_3$) δ4.50 (br s, 2 H, NH$_2$, D$_2$O exchangeable), 7.15 (d, 1 H, 3-H, J=6 Hz), 7.95 (d, 1H, 6-H, J=2 Hz). Analysis calculated for C$_5$H$_4$ClFN$_2$: C, 40.97; H, 2.75; N, 19.12. Found: C, 41.18; H, 2.39; N, 18.89.

2,5-Dichloropyridine-1-oxide (14). A mixture of 2,5-dichloropyridine (10 g, 67 mmol), 180 mL of trifluoroacetic acid and 22 mL of 50% hydrogen peroxide was heated at 70–75° C. with stirring until TLC showed the reaction to be complete. The reaction mixture was evaporated to dryness in vacuo and co-evaporated with water twice. The residue was stirred with 40 mL of water and 200 mL of methylene chloride and neutralized by dropwise addition of 28% ammonium hydroxide solution. The aqueous layer was further extracted with methylene chloride and the combined organic layer was dried, filtered and evaporated to give 10 g (91%) of product, which was used directly for the next step. A small sample was purified by silica gel column chromatography (CH$_2$Cl$_2$/EtOAc, 10:1, v/v, R$_f$0.24): mp 73–75° C.; $^1$H NMR (CDCl$_3$) δ7.13 (dd, 1 H, 4-H, J=10 Hz, 2 Hz), 7.45 (d, 1H, 3-H, J=10 Hz), 8.35 (d, 1 H, 6-H, J=2 Hz). Analysis calculated for C$_5$H$_3$Cl$_2$NO.0.5 H$_2$O: C, 36.62; H, 1.84; N, 8.54. Found: C, 36.43; H, 2.01; N, 8.25.

Compounds 15 and 16 were synthesized by methodology similar to that described for compounds 11 and 12, respectively.

2,5-Dichloro-4-nitropyridine-1-oxide (15). Compound 15 was isolated as light yellow crystals (6.5 g, 50.5%): mp 137–139° C.; $^1$H NMR (DMSO-d$_6$) δ8.70 (s, 1 H, 3-H), 9.05 (s, 1 H, 6-H). Analysis calculated for C$_5$H$_2$Cl$_2$N$_2$O$_3$: C, 28.73; H, 0.96; N, 13.41. Found: C, 28.39; H, 1.06; N, 13.55.

2,5-Dichloro-4-aminopyridine (16). Compound 16 was isolated as a white solid (4.0 g, 85%). mp 122–123° C.; $^1$H NMR (CDCl$_3$) δ4.75 (br s, 2 H, NH$_2$, D$_2$O exchangeable), 6.63 (s, 1 H, 3-H), 8.05 (s, 1H, 6-H). Analysis calculated for C$_5$H$_4$Cl$_2$N$_2$: C, 36.84; H, 2.47; N, 17.19. Found: C, 36.58; H, 2.30; N, 16.88.

EXAMPLE 3

Scheme 2

4-Nitramino-2,3,6-trifluoropyridine (17). 4-Amino-2,4,6-trifluoropyridine (3, 7 g, 47.3 mmol) was carefully added to 75 mL of concentrated sulfuric acid at 0–5° C. (ice-bath) with stirring to form a solution. Potassium nitrate (10.1 g, 100 mmol) was gradually added to the solution during a period of 20 min while the internal temperature was maintained below 5° C. The reaction mixture was further stirred at 0–5° C. for 1 h and at room temperature for 15 min, then poured onto 300 g of crushed ice. The resulting acidic solution was extracted with methylene chloride. The methylene chloride extracts were combined, dried, filtered and concentrated to give 8 g (88%) of product as a yellow solid. It was used directly for the next step in the reaction without further purification. A small analytical sample was purified by silica gel chromatography: mp 135–137° C.; $^1$H NMR (CDCl$_3$) δ7.55 (d, 1 H, 3-H, J=2 Hz), 10.70 (br s, 1H, NH, D$_2$O exchangeable). Analysis calculated for C$_5$H$_2$F$_3$N$_3$O$_2$: C, 31.10; H, 1.04; N, 21.76. Found: C, 31.23; H, 1.23; N, 21.60.

Compounds 18–21 were synthesized by methodology similar to that described for compound 17.

3-Chloro-2,6-difluoro-4-nitraminopyridine (18). Compound 18 was isolated as a light yellow solid (10.7 g, 76.4%): mp 100–102° C.; $^1$H NMR (CDCl$_3$) δ7.62 (d, 1 H, 5-H, J=2 Hz), 10.48 (br s, 1H, NH, D$_2$O exchangeable). Analysis calculated for C$_5$H$_2$ClF$_2$N$_3$O$_2$: C, 28.66; H, 0.96; N, 20.05. Found: C, 29.02; H, 1.25; N, 20.40.

2,6-Difluoro-4-nitraminopyridine (19). Compound 19 was isolated as an off-white solid (4.2s g, 76%): mp 140° C.

(dec.); $^1$H NMR (CDCl$_3$) δ6.96 (s, 2 H, 3- and 5-H), 7.62 (br s, 1H, NH, D$_2$O exchangeable). Analysis calculated for C$_5$H$_3$F$_2$N$_3$O$_2$: C, 34.30; H, 1.73; N, 24.00. Found: C, 34.42; H, 1.85; N, 24.05.

2-Chloro-5-fluoro-4-nitraminopyridine (20). Compound 20 was isolated as a light yellow solid (2.0 g, 83%): mp 160° C. (dec.); $^1$H NMR (CDCl$_3$) δ7.90 (s, 1H, 3-H), 8.32 (d, 1H, 6-H, J=2 Hz), 12.70 (br s, 1H, NH, D$_2$O exchangeable). Analysis calculated for C$_5$H$_3$ClFN$_3$O$_2$: C, 37.17; H, 3.12; N, 26.01. Found: C, 37.36; H, 3.16; N, 25.75.

2,5-Dichloro-4-nitraminopyridine (21). Compound 21 was isolated as a light yellow solid (1.2 g, 65%): mp 154° C. (dec.); $^1$H NMR (DMSO-d$_6$) δ6.90 (br s, 1H, NH, D$_2$O exchangeable), 7.85 (s, 1H, 3-H), 8.45 (s, 1H, 6-H). Analysis calculated for C$_5$H$_3$Cl$_2$N$_3$O$_2$: C, 28.87; H, 1.45; N, 20.20. Found: C, 28.55; H, 1.26; N, 20.45.

4-Amino-3-nitro-2,5,6-trifluoropyridine (22). 4-Nitramino-2,3,6-trifluoropyridine (17, 9.3 g, 48 mmol) was carefully added to 70 mL of concentrated sulfuric acid. The mixture was stirred at room temperature overnight (18 h), then poured onto 170 g of crushed ice with stirring. The resulting acidic solution was mixed with 100 mL of methylene chloride and neutralized by dropwise addition of 28% ammonium hydroxide with stirring while the internal temperature was maintained below 5° C. in a salted ice bath. The organic layer was separated and the aqueous layer was extracted with methylene chloride. The combined organic extracts were dried, filtered, evaporated in vacuo to dryness and purified by silica gel column chromatography (CH$_2$Cl$_2$/hexane, 1:1, v/v) to give 3.7 g (40%) of off-white crystals: mp 99–100° C.; $^1$H NMR (CDCl$_3$) δ6.80 (br s, 2H, 4-NH$_2$, D$_2$O exchangeable). Analysis calculated for C$_5$H$_2$F$_3$N$_3$O$_2$: C, 31.10; H, 1.04; N, 21.76. Found: C, 31.01; H, 1.34; N, 21.43.

Compounds 23–26 were synthesized by a procedure similar to that described for compound 22.

4-Amino-3-chloro-2,6-difluoro-5-nitropyridine (23). Compound 23 was isolated as an off-white solid (4.1 g, 82%): mp 84–85° C.; $^1$H NMR (CDCl$_3$) δ6.20 (br s, 2H, 4-NH$_2$, D$_2$O exchangeable). Analysis calculated for C$_5$H$_2$ClF$_2$N$_3$O$_2$: C, 28.66; H, 0.96; N, 20.05. Found: C, 28.99; H, 0.78; N, 19.66.

4-Amino-2,6-difluoro-5-nitropyridine (24). Compound 24 was isolated as an off-white solid (1.7 g, 89%): mp 149–150° C. (lit.[20] 147° C.); $^1$H NMR (DMSO-d$_6$) δ6.40 (s, 1 H, 5-H), 8.20 (br s, 2H, 4-NH$_2$, D$_2$O exchangeable).

4-Amino-2-chloro-5-fluoro-3-nitropyridine (25). Compound 25 was isolated as an off-white solid (1.7 g, 90%): mp 154–155° C.; $^1$H NMR (CDCl$_3$) δ6.70 (br s, 2 H, 4-NH$_2$, D$_2$O exchangeable), 8.00 (d, 1 H, 6-H, J=2 Hz). Analysis calculated for C$_5$H$_3$ClFN$_3$O$_2$: C, 31.35; H, 1.58; N, 21.94. Found: C, 31.55; H, 1.60; N, 21.77.

4-Amino-2,5-dichloro-3-nitropyridine (26). Compound 26 was isolated as an off-white solid (1.8 g, 97%): mp 168–170° C.; $^1$H NMR (DMSO-d$_6$) δ7.45 (br s, 2H, 4-NH$_2$, D$_2$O exchangeable), 8.20 (s, 1 H, 6-H). Analysis calculated for C$_5$H$_3$Cl$_2$N$_3$O$_2$: C, 28.87; H, 1.45; N, 20.20. Found: C, 28.60; H, 1.31; N, 20.02.

3,4-Diamino-2,5,6-trifluoropyridine (27). A mixture of 4-amino-3-nitro-2,5,6-trifluoropyridine (22, 1.08 g, 5.6 mmol) and 1.5 g of Raney nickel in 50 mL of anhydrous ethyl alcohol was hydrogenated at 36 psi in a Parr hydrogenation apparatus for 2 h. The catalyst was removed by filtration and washed carefully with ethyl alcohol. The filtrate and washings were combined and evaporated in vacuo to give 0.9 g (98%) of product as an off-white solid. A small analytical sample was purified by silica gel chromatography (CH$_2$Cl$_2$/EtOH, 20:1, v/v, R$_f$ 0.48) to give white crystals: mp 116–117° C.; $^1$H NMR (DMSO-d$_6$) δ3.35 (br s, 2 H, NH$_2$, D$_2$O exchangeable), 5.10 (br s, 2 H, NH$_2$, D$_2$O exchangeable). Analysis calculated for C$_5$H$_4$F$_3$N$_3$: C, 36.82; H, 2.47; N, 25.76. Found: C, 37.20; H, 2.59; N, 25.40.

Compounds 28–31 were synthesized by methodology similar to that described for compound 27.

5-Chloro-3,4-diamino-2,6-difluoropyridine (28). Compound 28 was isolated as a white solid (2.9 g, 92%): mp 178–179° C.; $^1$H NMR (DMSO-d$_6$) δ3.00 (br s, 2 H, NH$_2$, D$_2$O exchangeable), 4.80 (br s, 2 H, NH$_2$, D$_2$O exchangeable). Analysis calculated for C$_5$H$_4$ClF$_2$N$_3$: C, 33.44; H, 2.24; N, 23.40. Found: C, 33.80; H, 2.45; N, 23.03.

3,4-Diamino-2,6-difluoropyridine (29). Compound 29 was isolated as a white solid (3.3 g, 92%): mp 135–136° C. (lit. McNamara, D. J.; Cook, P. D. J. Med. Chem. 1987 30, 340–347; mp 132° C.); $^1$H NMR (DMSO-d$_6$) δ4.23 (br s, 2 H, NH$_2$, D$_2$O exchangeable), 6.05 (s, 1 H, 5-H), 6.20 (br s, 2 H, NH$_2$, D$_2$O exchangeable). Analysis calculated for C$_5$H$_5$F$_2$N$_3$: C, 41.38; H, 3.47; N, 28.96. Found: C, 41.10; H, 3.68; N, 28.64.

2-Chloro-3,4-diamino-5-fluoropyridine (30). Compound 30 was isolated as an off-white solid (1.4 g, 94%): mp 178–179° C.; $^1$H NMR (DMSO-d$_6$) δ4.95 (br s, 2 H, NH$_2$, D$_2$O exchangeable), 5.80 (br s, 2 H, NH$_2$, D$_2$O exchangeable), 7.42 (d, 1 H, 6-H, J=2 Hz). Analysis calculated for C$_5$H$_5$ClFN$_3$: C, 37.17; H, 3.12; N, 26.01. Found: C, 37.36; H, 3.16; N, 25.75.

3,4-Diamino-2,5-dichloropyridine (31). Compound 31 was isolated as a white solid (1.9 g, 94%): mp 197–199° C.; $^1$H NMR (DMSO-d$_6$) δ5.05 (br s, 2H, NH$_2$, D$_2$O exchangeable), 5.95 (br s, 2 H, NH$_2$, D$_2$O exchangeable), 7.45 (s, 1 H, 6-H). Analysis calculated for C$_5$H$_5$Cl$_2$N$_3$: C, 33.73; H, 2.83; N, 23.60. Found: C, 33.60; H, 3.11; N, 23.22.

4,6,7-Trifluoroimidazo[4,5-c]pyridine (32) and 1-[(1-acetyloxy-1-ethoxy)methyl]-4,6,7-trifluoroisssmidazo[4,5-c]pyridine (32a). A mixture of 3,4-diamino-2,5,6-trifluoropyridine (27, 0.9 g, 5.5 mmol) and 9 mL of diethoxymethyl acetate was heated at 100° C. for 1 h with exclusion of moisture. The reaction mixture was then evaporated to dryness in vacuo and the residue was purified on a silica gel column, eluted with CH$_2$Cl$_2$/EtOAc, first (10:1, v/v), then (1:1, v/v) to give compounds 32 (0.45 g, 47%) and 32a (0.45 g, 28%).

Compound 32 was isolated as white crystals: TLC, R$_f$ 0.35 (CH$_2$Cl$_2$/EtOH, 20:1, v/v); mp 182–184° C.; $^1$H NMR (DMSO-d$_6$) δ8.55 (s, 1 H, 2-H), 10.60 (br s, 1 H, NH, D$_2$O exchangeable). Analysis calculated for C$_6$H$_2$F$_3$N$_3$: C, 41.90; H, 1.16; N, 24.27. Found: C, 42.00; H, 1.42; N, 23.87.

Compound 32a was isolated as a syrup: TLC, R$_f$ 0.77 (CH$_2$Cl$_2$/EtOAc, 10:1, v/v); $^1$H NMR (CDCl$_3$) δ1.42 (t, 3 H, CH$_3$), 2.25 (s, 3 H, acetyl), 4.20 (m, 2 H, CH$_2$), 7.62 (s, 1 H, CH), 8.45 (d, 1 H, 2-H); MS, m/e 290 (M$^+$+1). Compound 32a in methylene chloride (30 mL) was treated with trimethylsilyl trifluoromethanesulfonate (1 mL). The mixture was stirred at room temperature overnight, then neutralized with 10% sodium bicarbonate solution and co-evaporated with 5 g of silica gel. The residue was purified by silica gel column chromatography to give 0.25 g of 32. The total yield of 32 was 0.7 g (74%).

Compounds 33–36 were synthesized by methodology similar to that described for compound 32. 7-Chloro-4,6-difluoroimidazo[4,5-c]pyridine (33). Compound 33 was isolated as off-white crystals (2.0 g, 74%): TLC, R$_f$ 0.45 (CH$_2$Cl$_2$/EtOH, 20:1, v/v); mp 225–227° C.; $^1$H NMR (DMSO-d$_6$) δ8.50 (s, 1 H, 2-H), 10.45 (br s, 1 H, NH, D$_2$O exchangeable). Analysis calculated for C$_6$H$_2$ClF$_2$N$_3$: C, 38.02; H, 1.06; N, 22.17. Found: C, 38.33; H, 1.08; N, 21.84.

1-[(1-Acetyloxy-1-ethoxy)methyl]-7-chloro-4,6-difluoroimidazo[4,5-c]pyridine (33a). Compound 33a was isolated as a syrup: TLC, $R_f$0.77 ($CH_2Cl_2$/EtOAc, 10:1, v/v); $^1H$ NMR ($CDCl_3$) δ1.40 (t, 3 H, $CH_3$), 2.23 (s, 3 H, acetyl), 4.18 (m, 2 H, $CH_2$), 7.58 (s, 1 H, CH), 8.42 (d, 1 H, 2-H); MS, m/e 307 ($M^+$+1).

4,6-Difluoroimidazo[4,5-c]pyridine (34). Compound 34 was isolated as a white solid (0.96 g, 90%): TLC, $R_f$0.35 ($CH_2Cl_2$/EtOH, 20:1, v/v); mp 170–171° C. (lit. Kroon, et al, *Rec. Trav. Chim.* 1976 95, 127–156; 169° C.); $^1H$ NMR (DMSO-$d_6$) δ7.15 (t, 1H, 2-H, J=1.5 Hz), 8.40 (s, 1 H, 7-H), 12.60 (br s, 1 H, NH, $D_2O$ exchangeable).

1-[(1-Acetyloxy-1-ethoxy)methyl]-4,6-difluoroimidazo[4,5-c]pyridine (34a). Compound 34a was isolated as a syrup: TLC, $R_f$0.84 ($CH_2Cl_2$/EtOH, 20:1, v/v); $^1H$ NMR ($CDCl_3$) δ1.30 (t, 3 H, $CH_3$), 2.20 (s, 3 H, acetyl), 3.90 (q, 2 H, $CH_2$), 7.05 (d, 1 H, 7H, J=2 Hz), 7.32 (s, 1 H, CH), 8.21 (d, 1 H, 2-H); MS, m/e 272 ($M^+$+1).

4-Chloro-7-fluoroimidazo[4,5-c]pyridine (35). Compound 35 was isolated as white crystals (1.11 g, 80%): TLC, $R_f$0.19 ($CH_2Cl_2$/EtOAc, 1:1, v/v); mp 232–234° C.; $^1H$ NMR (DMSO-$d_6$) δ8.12 (d, 1 H, 6-H, J=2 Hz), 8.56 (s, 1 H, 2-H), 13.80 (br s, 1 H, NH, $D_2O$ exchangeable). Analysis calculated for $C_6H_3ClFN_3$: C, 37.17; H, 3.12; N, 26.01. Found: C, 37.36; H, 3.16; N, 25.75.

1-[(1-Acetyloxy-1-ethoxy)methyl]-4-chloro-7-fluoroimidazo[4,5-c]pyridine (35a). Compound 35a was isolated as a syrup: TLC, $R_f$0.29 ($CH_2Cl_2$/EtOAc, 10:1, v/v); $^1H$ NMR ($CDCl_3$) δ1.37 (t, 3 H, $CH_3$), 2.20 (s, 3 H, acetyl), 3.95 (q, 2 H, $CH_2$), 7.57 (s, 1 H, CH), 8.15 (d, 1 H, 6-H, J=2 Hz), 8.35 (s, 1 H, 2-H); MS, m/e 289 ($M^+$+1).sss 4,7-Dichloroimidazo[4,5-c]pyridine (36). Compound 36 was isolated as a white solid (1.52 g, 80%): TLC, $R_f$0.0sss9 ($CH_2Cl_2$/EtOAc, 5:1, v/v); mp 270–272° C.; $^1H$ NMR (DMSO-$d_6$) δ8.25 (s, 1 H, 6-H), 8.60 (s, 1 H, 7-H), 13.60 (br s, 1 H, NH, $D_2O$ exchangeable). Analysis calculated for $C_6H_3Cl_2N_3$: C, 38.33; H, 1.61; N, 22.35. Found: C, 38.52; H, 1.90; N, 22.17.

1-[(1-Acetyloxy-1-ethoxy)methyl]-4,7-dichloroimidazo[4,5-c]pyridine (36a). Compound 36a was isolated as a syrup: TLC, $R_f$0.58 ($CH_2Cl_2$/EtOAc, 5:1, v/v); $^1H$ NMR ($CDCl_3$) δ1.32 (t, 3 H, $CH_3$), 2.15 (s, 3 H, acetyl), 4.10 (m, 2 H, $CH_2$), 7.95 (s, 1 H, CH), 8.25 (s, 1 H, 2-H), 8.44 (s, 1 H, 6-H); MS, m/e 304 ($M^+$+1).

EXAMPLE 4

Scheme 3

4,6-Difluoro-1-(2,3,5-tri-O-benzoyl-β-D-ribofuranosyl)imidazo[4,5-c]pyridine (37). A suspension of 4,6-difluoroimidazo[4,5-c]pyridine (34, 0.34 g, 2.2 mmol) in hexamethyldisilazane (10 mL) and ammonium sulfate (a catalytic amount) was refluxed for 2 h under anhydrous conditions. The resulting clear solution was cooled and concentrated in vacuo to yield the silylated base as a white solid, which was dissolved in 12 mL of dichloroethane. 1-O-Acetyl-2,3,5-O-benzoyl-D-ribofuranose (1.2 g, 2.4 mmol) was added to the solution, followed by 1 mL of TMSOTf and the reaction mixture was stirred at room temperature under nitrogen overnight. The reaction mixture was quenched by addition of a saturated sodium bicarbonate solution (10 mL) and further stirred for 10 minutes at room temperature. The organic layer was separated and the aqueous layer was extracted with methylene chloride (30 mL×2). The combined organic layers were washed with a saturated sodium bicarbonate solution, then water and dried (anhydrous $MgSO_4$). After filtration, the filtrate was concentrated in vacuo and the residue was purified by silica gel column chromatography ($CH_2Cl_2$/EtOAc, 30:1, v/v) to yield 37 (1.0 g, 77%) as a foam: $^1H$ NMR ($CDCl_3$) δ 4.62–4.82 (m, 3 H, 4'- and 5'-H), 5.85–5.92 (m, 2 H, 2'- and 3'-H), 6.20 (d, 1 H, 1'-H, J=5 Hz), 7.05 (d, 1 H, 7-H, J=1.5 Hz), 7.20–7.90 (m, 15 H, ArH), 8.15 (s, 1 H, 2-H). Analysis calculated for $C_{32}H_{23}F_2N_3O_7$: C, 64.10; H, 3.87; N, 7.01. Found: C, 64.28; H, 4.06; N, 6.93.

4-Amino-6-fluoro-1-(β-D-ribofuranosyl)imidazo[4,5-c]pyridine (38). A suspension of 4,6-difluoro-1-(2,3,5-tri-O-benzoyl-β-D-ribofuranosyl)imidazo[4,5-c]pyridine (37, 0.6 g, 1 mmol) in 50 mL of saturated ethanolic ammonia solution was stirred in a pressure bottle at room temperature for 4 days. The cooled reaction mixture was evaporated to dryness and the residue was purified by silica gel column chromatography ($CH_2Cl_2$/EtOH, 10:1, v/v) to give 0.2 g (70%) of product as a white solid: mp 171–172° C.; UV (MeOH) $\lambda_{max}$ 274 nm (ε 15,026), $\lambda_{min}$ 234 nm; UV (0.01 N HCl) $\lambda_{max}$ 276 nm (ε 11,863), $\lambda_{min}$ 236 nm; UV (0.01 N NaOH) $\lambda_{max}$ 274 nm (ε 14,027), $\lambda_{min}$ 232 nm; $^1H$ NMR (DMSO-$d_6$) δ3.63 (m, 2 H, 5'-H), 3.94 (m, 1 H, 4'-H), 4.10 (m, 1 H, 3'-H), 4.28 (m, 1 H, 2'-H), 5.12 t, 1 H, 5'-OH, $D_2O$ exchangeable), 5.20 (d, 1 H, OH, $D_2O$ exchangeable), 5.45 (d, 1 H, OH, $D_2O$ exchangeable), 5.71 (d, 1 H, 1'-H, J=6.0 Hz), 6.55 (d, 1 H, 7-H, J=1.5 Hz), 6.55 (br s, 2 H, 4-$NH_2$, $D_2O$ exchangeable), 8.25 (s, 1 H, 2-H). Analysis calculated for $C_{11}H_{13}FN_4O_4$: C, 46.48; H, 4.61; N, 19.70. Found: C, 46.12; H, 4.44; N, 19.39.

6-Fluoro-4-methylamino-1-(β-D-ribofuranosyl)imidazo[4,5-c]pyridine(39). A mixture of 4,6-difluoro-1-(2,3,5-tri-O-benzoyl-β-D-ribofuranosyl)imidazo[4,5-c]pyridine (37, 0.3 g, 0.5 mmol) and 10 mL of 40% methylamine was stirred at room temperature until TLC showed the reaction to be complete (about 3 days). The reaction mixture was evaporated to dryness and purified by silica gel column chromatography ($CH_2Cl_2$/EtOH, 10:1, v/v) to give 0.12 g (77%) of product as a white solid: mp 175–177° C.; UV (MeOH) $\lambda_{max}$ 280 nm (ε 19,306), $\lambda_{min}$ 238 nm; UV (0.01 N HCl) $\lambda_{max}$ 282 nm (ε 15,835), $\lambda_{min}$ 242 nm; UV (0.01 N NaOH) $\lambda_{max}$ 280 nm (ε 18,221), $\lambda_{min}$ 238 nm; $^1H$ NMR (DMSO-$d_6$) δ2.88 (d, 3 H, $CH_3$, J=4.5), 3.62 (m, 2 H, 5'-H), 3.75 (m, 1 H, 4'-H), 4.07 (m, 1 H, 3'-H), 4.26 (m, 1 H, 2'-H), 5.15 [t, 1 H, 5'-OH, $D_2O$ exchangeable), 5.20 (d, 1 H, OH, $D_2O$ exchangeable), 5.44 (d, 1 H, OH, $D_2O$ exchangeable), 5.71 (d, 1 H, 1'-H, J=6.3 Hz), 6.55 (d, 1 H, 7-H, J=1.5 Hz), 6.53 (br s, 1 H, 4-$NHCH_3$, $D_2O$ exchangeable), 8.25 (s, 1 H, 2-H). Analysis calculated for $C_{12}H_{15}FN_4O_4$: C, 48.32; H, 5.07; N, 18.78. Found: C, 47.94; H, 5.01; N, 18.39.

4-Amino-6-fluoro-1(2,3,5-tri-O-benzyl-β-D-arabinoffiinosyl)imidazo[4,5-c]pyridine (41) and 4-amino-6-fluoro-1-(2,3,5-tri-O-benzyl-α-D-arabinofuranosyl)imidazo[4,5-c]pyridine (42). A mixture of 4,6-difluoroimidazo[4,5-c]pyridine (34, 0.5 g, 3.2 mmol) and ammonium sulfate (a catalytic amount) in hexamethyldisilazane (15 mL) was refluxed for 2 h. The resulting clear solution was cooled and concentrated in vacuo under anhydrous conditions to dryness. The residue was dissolved in 15 mL of dichloroethane, followed by addition of 1-O-(4-nitrobenzoyl)-2,3,5-tri-O-benzyl-D-arabinofuranose (2 g, 3.6 mmol) and TMSOTf (1 mL) and the reaction mixture was refluxed with stirring under nitrogen for 2 h. The reaction mixture was cooled and stirred with saturated sodium bicarbonate solution (15 mL) for 10 min at room temperature. The organic layer was separated and the aqueous layer was extracted with methylene chloride (30 mL×2). The combined organic layer was washed with saturated sodium bicarbonate solution, then water and dried (anhydrous $MgSO_4$). After filtration, the filtrate was concentrated in vacuo and the residue was purified by silica gel column chromatography (CH₂Cl₂/EtOAc, 20:1, v/v) to yield 40 (1.2 g, 67%) as a syrup. NMR showed it to be a mixture of α- and β-anomers. Compound 40 (1.1 g, 2.0 mmol) was dissolved in 60 mL of ethanol, saturated with anhydrous ammonia and heated in a stainless steel bomb at 100–105° C. overnight. The reaction mixture was cooled, evaporated to dryness and separated by silica gel column chromatography (CH₂Cl₂/EtOH, 20:1, v/v) to yield 41 (0.30 g, 27%), 42 (0.34 g, 31%) and a mixture of 41 and 42 (0.17 g, 15%).

Compound 41 was isolated as a white foam: TLC, $R_f$ 0.63 (CH₂Cl₂/EtOH, 20:1, v/v); ¹H NMR (CDCl₃) δ 3.70 (m, 2 H, 5'-H), 4.10 (m, 1 H, 4'-H), 4.25 (m, 2 H, 2'- and 3'-H), 4.65 (s, 6 H, ArCH₂), 5.75 (br s, 2 H, NH₂, D₂O exchangeable), 5.96 (d, 1 H, 1'-H, J=5 Hz), 6.14 (s, 1 H, 7-H), 6.80–7.40 (m, 15 H, ArH), 8.01 (s, 1 H, 2-H). Analysis calculated for C₃₂H₃₁FN₄O₄: C, 69.28; H, 5.63; N, 10.10. Found: C, 69.10; H, 5.40; N, 9.96.

Compound 42 was isolated as a white foam: TLC, $R_f$ 0.53 (CH₂Cl₂/EtOH, 20:1, v/v); ¹H NMR (CDCl₃) δ 3.58 (m, 2 H, 5'-H), 4.25 (m, 1 H, 4'-H), 4.30 (m, 2 H, 2'- and 3'-H), 4.50 (s, 6 H, ArCH₂), 5.60 (br s, 2 H, NH₂, D₂O exchangeable), 5.85 (d, 1 H, 1'-H, J=5.2 Hz), 6.20 (s, 1 H, 7-H), 7.00–7.40 (m, 15 H, ArH), 7.84 (s, 1 H, 2-H). Analysis calculated for C₃₂H₃₁FN₄O₄·0.05EtOH: C, 69.01; H, 5.67; N, 10.06. Found: C, 68.87; H, 5.30; N, 9.98.

4-Amino-6-fluoro-1-β-D-arabinofuranosylimidazo[4,5-c]pyridine (43). A mixture of 4-amino-6-fluoro-1-(2,3,5-tri-O-benzyl-β-D-arabinofuranosyl)imidazo[4,5-c]pyridine (41, 0.15 g, 0.27 mmol), palladium (II) oxide hydrate (0.25 g), cyclohexene (20 mL) and ethanol (20 mL) was refluxed overnight. The reaction mixture was cooled, filtered and washed with ethanol. The combined filtrate and washings were evaporated in vacuo and the residue was purified by silica gel column chromatography (CH₂Cl₂/EtOH, 6:1, v/v) to give 45 mg (58%) of product as white crystals: mp 215° C. (dec.); UV (MeOH) $\lambda_{max}$ 274 nm (ε 14,127), $\lambda_{min}$ 234 nm; UV (0.01 N HCl) $\lambda_{max}$ 275 nm (ε 9,701), $\lambda_{min}$ 235 nm; UV (0.01 N NaOH) $\lambda_{max}$ 274 nm (ε 12,595), $\lambda_{min}$ 234 nm; ¹H NMR (DMSO-d₆) δ3.65 (m, 2 H, 5'-H), 3.73 (m, 1 H, 4'-H), 4.06 (m, 1 H, 3'-H), 4.15 (m, 1 H, 2'-H), 5.08 [t, 1 H, 5'-OH, D₂O exchangeable), 5.05 (d, 1 H, OH, D₂O exchangeable), 5.50 (d, 1 H, OH, D₂O exchangeable), 6.08 (d, 1 H, 1'-H, J=5.1 Hz), 6.42 (d, 1 H, 7-H, J=1.2 Hz), 6.59 (br s, 2 H, 4-NH₂, D₂O exchangeable), 8.17 (s, 1 H, 2-H). Analysis calculated for C₁₁H₁₃FN₄O₄: C, 46.48; H, 4.61; N, 19.70. Found: C, 46.70; H, 5.00; N, 19.35.

4-Amino-6-fluoro-1-α-D-arabinofuranosylimidazo[4,5-c]pyridine (44). This compound was synthesized by a procedure similar to that described for compound 43. Compound 44 was isolated as white crystals (60 mg, 65%): mp 198° C. (dec.); UV (MeOH) $\lambda_{max}$ 272 nm (ε 12,344), $\lambda_{min}$ 234 nm; UV (0.01 N HCl) $\lambda_{max}$ 274 nm (ε 10,232), $\lambda_{min}$ 234 nm; UV (0.01 N NaOH) $\lambda_{max}$ 274 nm (ε 11,532), $\lambda_{min}$ 234 nm; ¹H NMR (DMSO-d₆) δ3.52 (m, 2 H, 5'-H), 4.02 (m, 1 H, 4'-H), 4.08 (m, 1 H, 3'-H), 4.33 (m, 1 H, 2'-H), 4.90 (t, 1 H, 5'-OH, D₂O exchangeable), 5.50 (d, 1sH, OH, D₂O exchangeable), 5.72 (d, 1 H, 1'-H, J=5.4 Hz), 5.84 (d, 1 H, OH, D₂O exchangeable), 6.41 (d, 1 H, 7-H, J=1.5 Hz), 6.69 (br s, 2 H, 4-NH₂, D₂O exchangeable), 8.20 (s, 1 H, 2-H). Analysis calcssulated for C₁₁H₁₃FN₄O₄: C, 46.48; H, 4.61; N, 19.71. Found: C, 46.68; H, 4.87; N, 19.43.

EXAMPLE 5

Scheme 4

Compounds 45 and 46 were synthesized by methodology similar to that described for compound 37.

4-Chloro-7-fluoro-1-(2,3,5-tri-O-benzoyl-β-D-ribofuranosyl)imidazo[4,5-c]pyridine (45). Compound 45 was isolated as a white foam (0.77g, 61%): ¹H NMR (CDCl₃) δ4.82 (m, 2 H, 5'-H), 4.92 (m, 1 H, 4'-H), 5.94 (m, 2 H, 2'- and 3'-H), 6.58 (d, 1 H, 1'-H, J=5 Hz), 7.30–8.10 (m, 15 H, ArH), 8.13 (d, 1 H, 7-H, J=1.5 Hz), 8.27 (s, 1 H, 2-H). Analysis calculated for C₃₂H₂₃ClFN₃O₇: C, 62.39; H, 3.76; N, 6.82. Found: C, 62.12; H, 4.02; N, 6.63.

4,7-Dichloro-1-(2,3,5-tri-O-benzoyl-β-D-ribofuranosyl)imidazo[4,5-c]pyridine (46). Compound 46 was isolated as a foam (2.4 g, 47%): ¹H NMR (CDCl₃) δ4.75 (m, 2 H, 5'-H), 4.80 (m, 1 H, 4'-H), 5.95 (in, 1 H, 3'-H), 6.00 (m, 1 H, 2'-H), 7.15 (d, 1 H, 1'-H, J=6 Hz), 7.25–8.00 (in, 15 H, ArH), 8.15 (s, 1 H, 6-H), 8.40 (s, 1 H, 2-H). Analysis calculated for C₃₂H₂₃Cl₂N₃O₇: C, 60.87; H, 3.67; N, 6.66. Found: C, 61.10; H, 3.84; N, 6.30.

4-Chloro-7-fluoro-1-(β-D-ribofuranosyl)imidazo[4,5-c]pyridine (47). To a suspension of 4-chloro-7-fluoro-1-(2,3,5-tri-O-benzoyl-β-D-ribofuranosyl)imidazo[4,5-c]pyridine (45, 0.73 g, 1.2 mmol) in dry methanol (50 mL) was added sodium methoxide until pH 10 was reached. The reaction mixture was refluxed for 30 min, cooled, neutralized with glacial acetic acid, and evaporated to dryness. The residue was purified by silica gel column chromatography (CH₂Cl₂/EtOH, 10:1, v/v) to give 0.29 g (78%) as a white solid: mp 187–189° C.; ¹H NMR (DMSO-d₆) δ3.58 (m, 1 H, 5'-H_A), 3.70 (m, 1 H, 5'-H_B), 3.99 (m, 1 H, 4'-H), 4.13 (m, 1 H, 3'-H), 4.36 (m, 1 H, 2'-H), 5.16 (t, 1 H, 5'-OH, D₂O exchangeable), 5.28 (d, 1 H, OH, D₂O exchangeable), 5.63 (d, 1 H, OH, D₂O exchangeable), 6.03 (d, 1 H, 1'-H, J=5.1 Hz), 8.27 (d, 1 H, 6-H, J=2.1 Hz), 8.88 (s, 1 H, 2-H). Analysis calculated for C₁₁H₁₁ClFN₃O₄: C, 43.50; H, 3.65; N, 13.84. Found: C, 43.43; H, 3.26; N, 13.81.

4,7-Dichloro-1-(β-D-ribofuranosyl)imidazo[4,5-c]pyridine (48). Compound 48 was synthesized by a procedure similar to that described for compound 47 and was isolated as white crystals (0.2 g, 56%): mp 172–174° C.; ¹H NMR (DMSO-d₆) δ3.53 (m, 1 H, 5'-H_A), 3.65 (m, 1 H, 5'-H_B), 4.15 (m, 1 H, 4'-H), 4.28 (m, 1 H, 3'-H), 4.45 (m, 1 H, 2'-H), 4.94 (t, 1 H, 5'-OH, D₂O exchangeable), 5.27 (d, 1 H, OH, D₂O exchangeable), 5.43 (d, 1 H, OH, D₂O exchangeable), 6.79 (d, 1 H, 1'-H, J=5.1 Hz), 8.27 (s, 1 H, 6-H), 8.72 (s, 1 H, 2-H). Analysis calculated for C₁₁H₁₁Cl₂N₃O₄: C, 41.27; H, 3.46; N, 13.13. Found: C, 41.00; H, 3.57; N, 12.91.

4-Amino-7-fluoro-1-(β-D-ribofuranosyl)imidazo[4,5-c]pyridine (51). A suspension of 4-chloro-7-fluoro-1-(β-D-ribofuranosyl)imidazo[4,5-c]pyridine (47, 0.51 g, 1.7 mmol) in 30 mL of anhydrous hydrazine was refluxed for 1 h. The reaction mixture was evaporated in vacuo to dryness and the residue was co-evaporated with ethanol (30 mL) and deoxygenated water twice (2×30 mL). The residue was dissolved in 40 mL of deoxygenated water containing 3.0 g (wet weight) of Raney Nickel and was refluxed with stirring under hydrogen (1 atm) for 8 h. The reaction mixture was filtered through Celite while hot, and the catalyst was washed with hot deoxygenated water. The combined filtrate and washings were evaporated in vacuo to dryness. The residue was purified by silica gel column chromatography (CH₂Cl₂/EtOH, 6:1, v/v) to give 0.26 g (54%) of product as a white solid: mp 160–161° C.; UV (MeOH) $\lambda_{max}$ 270 nm (ε 7,145), $\lambda_{min}$ 238 nm; UV (0.01 N HCl) $\lambda_{max}$ 268 nm (ε 8,077), $\lambda_{min}$ 238 nm; UV (0.01 N NaOH) $\lambda_{max}$ 268 nm (ε 7,445), $\lambda_{min}$ 238 nm; ¹H NMR (DMSO-d₆) δ3.58 (m, 1 H, 5'-H_A), 3.62 (m, 1 H, 5'-H_B), 3.94 (m, 1 H, 4'-H), 4.10 (m, 1 H, 3'-H), 4.35 (m, 1 H, 2'-H), 5.07 (t, 1 H, 5'-OH, D₂O exchangeable), 5.24 (d, 1 H, OH, D₂O exchangeable), 5.54 (d, 1 H, ssOH, D₂O exchangeable), 5.91 (d, 1 H, 1'-H, J=5.1 Hz), 6.22 (br s, 2 H, NH₂, D₂O exchangeable), 7.67 (d, 1 H, 6-H, J=2.1 Hz), 8.48 (s, 1 H, 2-H). Analysis calculated for $C_{11}H_{13}FN_4O_4$: C, 46.48; H, 4.61; N, 19.71. Found: C, 46.52; H, 4.50; N, 19.50.

4-Amino-7-chloro-1-(β-D-ribofuranosyl)imidazo[4,5-c]pyridine (52). Compound 52 was synthesized by a procedure similar to that described for compound 51 and was isolated as a white solid (0.14 g, 49%): mp 169° C. (dec); UV (MeOH) $\lambda_{max}$ 271 nm (ε 7,010), $\lambda_{min}$ 237 nm; UV (0.01 N HCl) $\lambda_{max}$ 269 nm (ε 7,900), $\lambda_{min}$ 236 nm; UV (0.01 N NaOH) $\lambda_{max}$ 269 nm (ε 7,400), $\lambda_{min}$ 236 nm; $^1$H NMR (DMSO-$d_6$) δ3.45 (m, 1 H, 5'-$H_A$), 3.56 (m, 1 H, 5'-$H_B$), 4.12 (m, 1 H, 4'-H), 4.20 (m, 1 H, 3'-H), 4.34 (m, 1 H, 2'-H), 4.92 (t, 1 H, 5'-OH, $D_2O$ exchangeable), 5.27 (d, 1 H, OH, $D_2O$ exchangeable), 5.61 (d, 1 H, OH, $D_2O$ exchangeable), 6.08 (br s, 2 H, $NH_2$, $D_2O$ exchangeable), 6.41 (d, 1 H, 1'-H, J=4.5 Hz), 7.72 (s, 1 H, 6-H), 8.41 (s, 1 H, 2-H). Analysis calculated for $C_{11}H_{13}ClN_4O_4$: C, 43.93; H, 4.36; N, 18.63. Found: C, 43.70; H, 4.32; N, 18.51.

EXAMPLE 6
Scheme 5

Compounds 53–56 were synthesized by methodology similar to that described for compound 37.

4,6,7-Trifluoro-1-(2,3,5-tri-O-benzoyl-β-D-ribofuranosyl)imidazo[4,5-c]pyridine (53). Compound 53 was isolated as a foam (0.76 g, 36%): TLC, $R_f$0.47 ($CH_2Cl_2$/EtOAc, 30:1, v/v); $^1$H NMR ($CDCl_3$) δ4.80–4.90 (m, 3 H, 4'- and 5'-H), 5.94 (m, 2 H, 2'- and 3'-H), 6.55 (d, 1 H, 1'-H, J=5.2 Hz), 7.30–8.05 (m, 15 H, ArH), 8.25 (s, 1 H, 2-H). Analysis calculated for $C_{32}H_{22}F_3N_3O_7$: C, 62.24; H, 3.59; N, 6.80. Found: C, 62.25; H, 3.49; N, 6.51.

4,6,7-Trifluoro-3-(2,3,5-tri-O-benzoyl-β-D-ribofuranosyl)imidazo[4,5-c]pyridine (54). Compound 54 was isolated as a foam (0.53 g, 25%): TLC, $R_f$0.55 ($CH_2Cl_2$/EtOAc, 30:1, v/v); $^1$H NMR ($CDCl_3$) δ4.80–4.92 (m, 3 H, 4'- and 5'-H), 5.95 (m, 2 H, 2'- and 3'-H), 6.53 (d, 1 H, 1'-H, J=5.5 Hz), 7.30–8.20 (m, 15 H, ArH), 8.43 (s, 1 H, 2-H). Analysis calculated for $C_{32}H_{22}F_3N_3O_7$: C, 62.24; H, 3.59; N, 6.80. Found: C, 62.06; H, 3.31; N, 6.69.

7-(Chloro-4,6-difluoro-1-(2,3,5-tri-O-benzoyl-β-D-ribofuranosyl)imidazo[4,5-c]pyridine (55). Compound 55 was isolated as a foam (0.57 g, 34%): TLC, $R_f$0.38 ($CH_2Cl_2$/EtOAc, 30:1, v/v); $^1$H NMR ($CDCl_3$) δ4.78–4.90 (m, 3 H, 4'- and 5'-H), 5.97 (m, 2 H, 2'- and 3'-H), 6.50 (d, 1 H, 1'-H, J=5.1 Hz), 7.30–8.12 (m, 15 H, ArH), 8.35 (s, 1 H, 2-H). Analysis calculated for $C_{32}H_{22}ClF_2N_3O_7$: C, 60.62; H, 3.50; N, 6.63. Found: C, 60.46; H, 3.40; N, 6.49.

7-Chloro-4,6-difluoro-3-(2,3,5-tri-benzoyl-β-D-ribofuranosyl)imidazo[4,5-c]pyridine (56). Compound 56 was isolated as a foam (0.50 g, 26%): TLC, $R_f$0.47 ($CH_2Cl_2$/EtOAc, 30:1, v/v); $^1$H NMR ($CDCl_3$) δ4.77–4.85 (m, 3 H, 4'- and 5'-H), 5.92 (m, 2 H, 2'- and 3'-H), 6.50 (d, 1 H, 1'-H, J=5.2 Hz), 7.25–8.15 (m, 15 H, ArH), 8.40 (s, 1 H, 2-H). Analysis calculated for $C_{32}H_{22}ClF_2N_3O_7$: C, 60.62; H, 3.50; N, 6.63. Found: C, 60.87; H, 3.39; N, 6.52.

Compounds 57–60 were synthesized by methodology similar to that described for compound 38.

4-Amino-6,7-difluoro-1-(β-D-ribofuranosyl)imidazo[4,5-c]pyridine (57). Compound 57 was isolated as a white solid (0.17 g, 77%): mp 163–165° C.; UV (MeOH) $\lambda_{max}$ 274 nm (ε 13,510), $\lambda_{min}$ 232 nm; UV (0.01 N HCl) $\lambda_{max}$ 274 nm (ε 12,256), $\lambda_{min}$ 232 nm; UV (0.01 N NaOH) $\lambda_{max}$ 274 nm (ε 11,421), $\lambda_{min}$ 232 nm; $^1$H NMR (DMSO-$d_6$) δ3.65 (m, 1 H, 5'-$H_A$), 3.67 (m, 1 H, 5'-$H_B$), 3.93 (m, 1 H, 4'-H), 4.02 (m, 1 H, 3'-H), 4.32 (m, 1 H, 2'-H), 5.07 (t, 1 H, 5'-OH, $D_2O$ exchangeable), 5.22 (d, 1 H, OH, $D_2O$ exchangeable), 5.54 (d, 1 H, OH, $D_2O$ exchangeable), 5.87 (d, 1 H, 1'-H, J=5.6 Hz), 6.65 (br s, 2 H, $NH_2$, $D_2O$ exchangeable), 8.43 (s, 1 H, 2-H). Analysis calculated for $C_{11}H_{12}F_2N_4O_4$: C, 43.71; H, 4.00; N, 18.54. Found: C, 43.92; H, 3.91; N, 18.59.

4-Amino-6,7-difluoro-3-(β-D-ribofuranosyl)imidazo[4,5-c]pyridine (58). Compound 58 was isolated as a white solid (0.14 g, 88%): mp 155–157° C.; UV (MeOH) $\lambda_{max}$ 292 nm (ε 5,742), $\lambda_{min}$ 264 nm; UV (0.01 N HCl) $\lambda_{max}$ 292 nm (ε 6,045), $\lambda_{min}$ 262 nm; UV (0.01 N NaOH) $\lambda_{max}$ 292 nm (ε 5,440), $\lambda_{min}$ 262 nm; $^1$H NMR (DMSO-$d_6$) δ3.65 (m, 1 H, 5'-$H_A$), 3.68 (m, 1 H, 5'-$H_B$), 4.01 (m, 1 H, 4'-H), 4.11 (m, 1 H, 3'-H), 4.22 (m, 1 H, 2'-H), 5.13 (t, 1 H, 5'-OH, $D_2O$ exchangeable), 5.20 (d, 1 H, OH, $D_2O$ exchangeable), 5.30 (d, 1 H, OH, $D_2O$ exchangeable), 5.90 (d, 1 H, 1'-H, J=6.6 Hz), 6.34 (br s, 2 H, $NH_2$, $D_2O$ exchangeable), 8.54 (s, 1 H, 2-H). Analysis calculated for $C_{11}H_{12}F_2N_4O_4$: C, 43.71; H, 4.00; N, 18.54. Found: C, 43.90; H, 4.02; N, 18.16.

4-Amino-7-chloro-6-fluoro-1-(β-D-ribofuranosyl)imidazo[4,5-c]pyridine (59). Compound 59 was isolated as a white solid (0.10 g, 85%): mp 175–177° C.; UV (MeOH) $\lambda_{max}$ 274 nm (ε 14,503), $\lambda_{min}$ 234 nm; UV (0.01 N HCl) $\lambda_{max}$ 274 nm (ε 12,997), $\lambda_{min}$ 236 nm; UV (0.01 N NaOH) $\lambda_{max}$ 274 nm (δ 15,367), $\lambda_{min}$ 235 mm; $^1$H NMR (DMSO-$d_6$) δ3.52 (m, 1 H, 5'-$H_A$), 3.62 (m, 1 H, 5'-$H_B$), 3.95 (m, 1 H, 4'-H), 4.10 (m, 1 H, 3'-H), 4.37 (m, 1 H, 2'-H), 5.12 (t, 1 H, 5'-OH, $D_2O$ exchangeable), 5.22 (d, 1 H, OH, $D_2O$ exchangeable), 5.58 (d, 1 H, OH, $D_2O$ exchangeable), 6.34 (d, 1 H, 1'-H, J=4.5 Hz), 6.94 (br s, 2 H, $NH_2$, $D_2O$ exchangeable), 8.51 (s, 1 H, 2-H). Analysis calculated for $C_{11}H_{12}ClFN_4O_4$: C, 41.45; H, 3.80; N, 17.58. Found: C, 41.17; H, 4.00; N, 17.35.

4-Amino-7-chloro-6-fluoro-3-(β-D-ribofuranosyl)imidazo[4,5-c]pyridine (60). Compound 60 was isolated as a white solid (0.13 g, 53%): mp 166–168° C.; UV (MeOH) $\lambda_{max}$ 292 nm (ε 8,631), $\lambda_{min}$ 268 nm; UV (0.01 N HCl) $\lambda_{max}$ 292 nm (ε 8,465), $\lambda_{min}$ 266 nm; UV (0.01 N NaOH) $\lambda_{max}$ 292 nm (ε 7,967), $\lambda_{min}$ 268 nm; $^1$H NMR (DMSO-$d_6$) δ3.55 (m, 1 H, 5'-$H_A$), 3.65 (m, 1 H, 5'-$H_B$), 3.98 (m, 1 H, 4'-H), 4.11 (m, 1 H, 3'-H), 4.20 (m, 1 H, 2'-H), 5.25 (t, 1 H, 5'-OH, $D_2O$ exchangeable), 5.35 (d, 1 H, OH, $D_2O$ exchangeable), 5.65 (d, 1 H, OH, $D_2O$ exchangeable), 5.87 (d, 1 H, 1'-H, J=6.6 Hz), 6.63 (br s, 2 H, $NH_2$, $D_2O$ exchangeable), 8.55 (s, 1 H, 2-H). Analysis calculated for $C_{11}H_{12}ClFN_4O_4$: C, 41.45; H, 3.80; N, 17.58. Found: C, 41.31; H, 4.10; N, 17.27.

EXAMPLE 7
Scheme 6

6-Amino-7-chloro-1,5-dihydro-1-β-D-ribofuranosylimidazo[4,5-c]pyridin-4-one (3-chloro-3-deazaguanosine, 61). To a stirred suspension of 3-deazaguanosine (see, Chiang, et al., *Biochem. Biophys. Res. Commun.* 1978 82, 417–423 and Secrist, et al.,*J. Med. Chem.* 1993 36, 2102–2106 (0.25 g, 0.9 mmol) in 7 mL of water was added N-chlorosuccimide (0.14 g, 1.0 mmol) at 0–5° C. in an ice-water bath. The reaction mixture was stirred at 0–5° C. for 1 h. The solid was collected, washed with cold water and then cold acetone. Crystallization from water provided 0.12 g (42%) of product: mp 195–196° C. (dec.); UV (MeOH) $\lambda_{max}$ 273 nm (ε 11,000), $\lambda_{min}$ 238 nm; UV (0.01 N HCl) $\lambda_{max}$ 285 nm (ε 13,200), $\lambda_{min}$ 242 nm; UV (0.01 N NaOH) $\lambda_{max}$ 274 nm (ε 11,200), $\lambda_{min}$ 240 nm; $^1$H NMR (DMSO-$d_6$) δ3.52 (m, 2 H, 5'-H), 3.90 (m, 1 H, 4'-H), 4.10 (m, 1 H, 3'-H), 4.25 (m, 1 H, 2'-H), 5.02 (d, 1 H, OH, $D_2O$ exchangeable), 5.10 (t, 1 H, OH, $D_2O$ exchangeable), 5.40 (d, 1 H, OH, $D_2O$ exchangeable), 5.70 (br s, 2 H, $NH_2$, $D_2O$ exchangeable), 6.25 (d, 1 H, 1'-H, J=7.0 Hz), 8.10 (s, 1 H, 2-H), 10.70 (br s, 1 H, NH, $D_2O$ exchangeable). Analysis calculated for $C_{11}H_{13}ClN_4O_5$: C, 41.71; H, 4.14; N, 17.69. Found: C, 41.80; H, 4.00; N, 17.38.

6-Amino-7-bromo-1,5-dihydro-1-β-D-ribofuranosylimidazo[4,5-c]pyridin-4-one (3-bromo-3-deazaguanosine, 62). To a stirred suspension of 3-deazaguanosine, prepared according to the method of Chiang, et al. and Secrist, et al., supra, (0.5 g, 1.8 mmol) in 6 mL of water was added gradually 12 mL of saturated bromine-water at such a rate that the yellow color of the reaction mixture disappeared between each addition (about 5 min). The reaction mixture was stirred for another 5 min and the solid was collected by filtration, and washed with cold water and cold acetone. The solid was crystallized from water to give 0.45 g (70%) of product: mp 174° C. (dec.); UV (MeOH) $\lambda_{max}$ 274 nm ($\epsilon$ 11,200), $\lambda_{min}$ 240 nm; UV (0.01 N HCl) $\lambda_{max}$ 284 nm ($\epsilon$ 13,200), $\lambda_{min}$ 238 nm; UV (0.01 N NaOH) $\lambda_{max}$ 274 nm ($\epsilon$ 11,600), $\lambda_{min}$ 240 nm; $^1$H NMR (DMSO-$d_6$) δ3.50 (m, 2 H, 5'-H), 3.80 (m, 1 H, 4'-H), 4.05 (m, 1 H, 3'-H), 4.28 (m, 1 H, 2'-H), 5.20–5.40 (br s, 2 H, OH, $D_2O$ exchangeable), 5.40 (t, 1 H, OH, $D_2O$ exchangeable), 5.62 (br s, 2 H, $NH_2$, $D_2O$ exchangeable), 6.38 (d, 1 H, 1'-H, J=6.8 Hz), 8.12 (s, 1 H, 2-H), 10.62 (br s, 1 H, NH, $D_2O$ exchangeable). Analysis calculated for $C_{11}H_{13}BrN_4O_5$: C, 36.58; H, 3.62; N, 15.51. Found: C, 36.41; H, 3.43; N, 15.23.

What is claimed is:

1. A compound according to the formula:

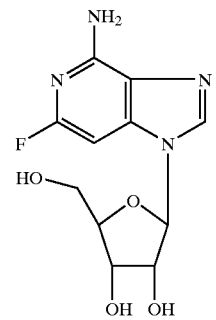

or its pharmaceutically acceptable salt.

2. A pharmaceutical composition comprising an effective amount of a compound according to claim 1 in combination with a pharmaceutically acceptable carrier, additive or excipient.

* * * * *